United States Patent
Dou et al.

(10) Patent No.: US 10,682,362 B2
(45) Date of Patent: Jun. 16, 2020

(54) TREATMENTS AND DIAGNOSTICS FOR CANCERS

(71) Applicant: Wayne State University, Detroit, MI (US)

(72) Inventors: Qingping Dou, Grosse Pointe, MI (US); Huanjie Yang, Windsor (CA); Elisabeth I. Heath, Bloomfield Hills, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/764,837

(22) PCT Filed: Oct. 14, 2016

(86) PCT No.: PCT/US2016/057210
§ 371 (c)(1),
(2) Date: Mar. 29, 2018

(87) PCT Pub. No.: WO2017/066697
PCT Pub. Date: Apr. 20, 2017

(65) Prior Publication Data
US 2018/0280412 A1    Oct. 4, 2018

Related U.S. Application Data

(60) Provisional application No. 62/259,426, filed on Nov. 24, 2015, provisional application No. 62/241,574, filed on Oct. 14, 2015.

(51) Int. Cl.
| | | |
|---|---|---|
| *A61K 31/58* | (2006.01) | |
| *A61P 35/00* | (2006.01) | |
| *A61K 38/00* | (2006.01) | |
| *A61K 38/05* | (2006.01) | |
| *G01N 33/574* | (2006.01) | |
| *A61K 31/69* | (2006.01) | |

(52) U.S. Cl.
CPC .............. *A61K 31/58* (2013.01); *A61K 31/69* (2013.01); *A61K 38/005* (2013.01); *A61K 38/05* (2013.01); *A61P 35/00* (2018.01); *G01N 33/57434* (2013.01); *G01N 2333/47* (2013.01); *G01N 2333/4703* (2013.01); *G01N 2333/723* (2013.01); *G01N 2333/91275* (2013.01); *G01N 2800/52* (2013.01)

(58) Field of Classification Search
CPC ..... A61K 31/58; A61K 31/69; A61K 2300/00
See application file for complete search history.

(56) References Cited

U.S. PATENT DOCUMENTS

| | | |
|---|---|---|
| 2005/0246794 A1 | 11/2005 | Khvorova et al. |
| 2008/0280864 A1 | 11/2008 | Brodie et al. |
| 2010/0048913 A1 | 2/2010 | Brodie et al. |
| 2014/0107180 A1* | 4/2014 | MacLeod ........... C12N 15/1138 514/44 A |
| 2014/0170157 A1 | 6/2014 | Agarwal et al. |
| 2014/0199236 A1 | 7/2014 | Chen et al. |
| 2014/0288037 A1 | 9/2014 | Casebier et al. |
| 2014/0370528 A1 | 12/2014 | Brnjic et al. |
| 2015/0005265 A1 | 1/2015 | Stewart |
| 2015/0110814 A1 | 4/2015 | Olson et al. |

FOREIGN PATENT DOCUMENTS

| | | |
|---|---|---|
| WO | WO2014152640 A1 | 9/2014 |
| WO | WO2014153215 A1 | 9/2014 |

OTHER PUBLICATIONS

Kraft et al. Cancer Biology & Therapy, (2011), 12(2), p. 119-124.*
Milacic et al., Int. J. Oncol., (2009), 35(6), p. 1481-1491.*
Kraft, et al., "Combination therapy of recurrent prostate cancer with the proteasome inhibitor bortezomib plus hormone blockade", Cancer Biology & Therapy, vol. 12, No. 2, 2011, pp. 119-124.
Milacic, et al., "Novel 8-hydroxylquinoline analogs induce copper-dependent proteasome inhibition and cell death in human breast cancer cells", Int. J. Oncol., vol. 35, No. 6, 2009, pp. 1481-1491.
Search Report and Written Opinion dated Dec. 28, 2016 for International Application No. PCT/US2016/057210.
Antonarakis et al., "AR-V7 and Resistance to Enzalutamide and Abiraterone in Prostate Cancer," N. Engl. J. Med., vol. 371, No. 11, 2014, pp. 1028-1038.
Banerjee & Liefshitz, "Potential of the Proteasomal Inhibitor MG-132 as an Anticancer Agent, Alone and in Combination," Anticancer Res., vol. 21, No. 6A, 2001, pp. 3941-3947.
Bizat et al., "Calpain is a Major Cell Death Effector in Selective Striatal Degeneration Induced In Vivo by 3-Nitropropionate: Implications for Huntington's Disease," J. Neurosci., vol. 23, No. 12, 2003, pp. 5020-5030.
Chen et al., "Bortezomib as the First Proteasome Inhibitor Anticancer Drug: Current Status and Future Perspectives," Curr. Cancer Drug Targets, vol. 11, No. 3, 2011, pp. 239-253.
Chen et al., "Clioquinol, a Therapeutic Agent for Alzheimer's Disease, Has Proteasome-Inhibitory, Androgen Receptor-Suppressing, Apoptosis-Inducing, and Antitumor Activities in Human Prostate Cancer Cells and Xenografts," Cancer Res., vol. 67, No. 4, 2007, pp. 1636-1644.
Chen et al., "Inhibition of the Proteasome Activity by Gallium(III) Complexes Contributes to Their Anti Prostate Tumor Effects," Cancer Res., vol. 67, No. 19, 2007, pp. 9258-9265.

(Continued)

*Primary Examiner* — Yong L Chu
(74) *Attorney, Agent, or Firm* — Lee & Hayes, P.C.; C. Rachal Winger; Tanya M. Harding

(57) ABSTRACT

Treatments and diagnostics for treatment efficacy against solid and liquid cancers are described. The treatments utilize a combination therapy of Galeterone and a proteasome inhibitor. The diagnostics can measure androgen receptor (AR) cleavage products including AR-variant 7 (AR-V7) cleavage products, Poly (ADP-ribose) polymerase (PARP) cleavage products, and/or Spectrin α2 cleavage products or inhibition of DUB activities from a blood sample to monitor treatment efficacy for castration-resistant prostate cancer (CRPC) or multiple myeloma (MM).

17 Claims, 26 Drawing Sheets
Specification includes a Sequence Listing.

(56) References Cited

OTHER PUBLICATIONS

Dou & Zonder, "Overview of Proteasome Inhibitor-Based Anti-Cancer Therapies: Perspective on Bortezomib and Second Generation Proteasome Inhibitors Versus Future Generation Inhibitors of Ubiquitin-Proteasome System," Curr. Cancer Drug Targets, vol. 14, No. 6, 2014, pp. 517-536.

Farshi et al., "Deubiquitinases (DUBs) and DUB Inhibitors: A Patent Review," Expert Opin. Ther. Pat., vol. 25, No. 10, 2015, pp. 1191-1208.

Frezza et al., "Modulation of the Tumor Cell Death Pathway by Androgen Receptor in Response to Cytotoxic Stimuli," J. Cell. Physiol., vol. 226, No. 11, 2011, pp. 2731-2739.

Gao & Dou, "N-Terminal Cleavage of Bax by Calpain Generates a Potent Propoptotic 18-kDa Fragment That Promotes bc1-2-Independent Cytochrome C Release and Apoptotic Cell Death," J. Cell. Biochem., vol. 80, No. 1, 2000, pp. 53-72.

Guo et al., "A Novel Androgen Receptor Splice Variant is Up-Regulated During Prostate Cancer Progression and Promotes Androgen Depletion-Resistant Growth," Cancer Res., vol. 69, No. 6, 2009, pp. 2305-2313.

Hu et al., "Ligand-Independent Androgen Receptor Variants Derived From Splicing of Cryptic Exons Signify Hormone-Regractory Prostate Cancer," Cancer Res., vol. 69, No. 1, 2009, pp. 16-22.

Kwegyir-Afful, et al., "Galeterone and VNPT55 Induce Proteasomal Degradation of AR/AR-V7, Induce Significant Apoptosis Via Cytochrome C Release and Suppress Growth of Castration Resistant Prostate Cancer Xenografts In Vivo," Oncotarget., vol. 6, No. 29, 2015, pp. 27440-27460.

Li et al., "A Patent Review of the Ubiquitin Ligase System: 2015-2018," Expert Opin. Ther. Pat., vol. 28, No. 12, 2018, pp. 919-937.

Liu et al.' "A Novel Proteasome Inhibitor Suppresses Tumor Growth Via Targeting Both 19S Proteasome . Deubiquitinases and 20S Proteolytic Peptidases," Sci. Rep., Vol. 4, No. 5240, 2014, pp. 1-13.

Njar and Brodie, "Discovery and Development of Galeterone (TOK-001 or VN/124-1) for the Treatment of all Stages of Prostate Cancer," J. Med. Chem., vol. 58, No. 5, 2015, pp. 2077-2087.

Patel et al., "Discovering Proteasomal Deubiquitinating Enzyme Inhibitors for Cancer Therapy: Lessons From Rational Design, Nature and Old Drug Reposition," Future Med. Chem., vol. 10, No. 17, 2018, pp. 2087-2108.

Pelley et al., "Calmodulin-Androgen Receptor (AR) Interaction: Calcium-Dependent, Calpain-Mediated Breakdown of AR in LNCaP Prostate Cancer Cells," Cancer Res., vol. 66, No. 24, 2006, pp. 11754-11762.

Pink et al., "Activation of a Cysteine Protease in MCF-7 and T47D Breast Cancer Cells During Beta-Lapachone-Vlediated Apoptosis," Exp. Cell. Res., vol. 255, No. 2, 2000, pp. 144-155.

Pom-Ares et al., "Cleavage of the Calpain Inhibitor, Calpastatin, During Apoptosis," Cell. Death Differ., vol. 5, No. 12, 1998, pp. 1028-1033.

Purushottamachar et al., "Systematic Structure Modification of Multitarget Prostate Cancer Drug Candidate Galeterone to Produce Novel Androgen Receptor Down-Regulating Agents as an Approach to Treatment of Advanced Prostate Cancer," J. Med. Chem., vol. 56, No. 12, 2013, pp. 4880-4898.

Shen et al., "The Interplay of AMP-Activated Protein Kinase and Androgen Receptor in Prostate Cancer Cells," J. Cell. Physiol., vol. 229, No. 6, 2014, pp. 688-695.

Soave et al., "Targeting the Ubiquitin-Proteasome System for Cancer Treatment: Discovering Novel Inhibitors From Nature and Drug Repurposing," Cancer Metastasis Rev., vol. 36, No. 4, 2017, pp. 717-736.

Tsubuki, et al., "Differential Inhibition of Calpain and Proteasome Activities by Peptidyl Aldehydes of Di-Leucine and Tri-Leucine," J. Biochem., vol. 119, No. 3, 1996, pp. 572-576.

Yang et al., "Calpain-Mediated Androgen Receptor Breakdown in Apoptotic Prostate Cancer Cells," J. Cell. Physiol., vol. 217, No. 3, 2008, pp. 569-576.

Yang et al., "Celastrol, a Triterpene Extracted From the Chinese "Thunder of God Vine," is a Potent Proteasome.Inhibitor and Suppresses Human Prostate Cancer Growth in Nude Mice," Cancer Res., vol. 66, No. 9, 2006, pp. 4758-4765.

Yang et al., "Pristimerin Induces Apoptosis by Targeting the Proteasome in Prostate Cancer Cells," J. Cell. Biochem., vol. 103, No. 1, 2008, pp. 234-244.

Yang et al., "Shikonin Exerts Antitumor Activity Via Proteasome Inhibition and Cell Death Induction In Vitro and In Vivo," Int. J. Cancer, vol. 124, No. 10, 2009, pp. 2450-2459.

Yang et al., "The Tumor Proteasome is a Primary Target for the Natural Anticancer Compound Withaferin a Isolated from "Indian Winter Cherry"," Mol. Pharmacol., vol. 71, No. 2, 2007, pp. 426-437.

Zhang et al., "Multiple Alphall-Spectrin Breakdown Products Distinguish Calpain and Caspase Dominated Necrotic and Apoptotic Cell Death Pathways," Apoptosis., vol. 14, No. 11, 2009, pp. 1289-1298.

* cited by examiner

FIG. 6

MEVQLGLGRVYPRPPSKTYRGAFQNLFQSVREVIQN
PGPRHPEAASAAPPGASLLLLQQQQQQQQQQQQQ
QQQQQQQETSPRQQQQQQGEDGSPQAHRRGPTG
YLVLDEEQQPSQPQSALECHPERGCVPEPGAAVAAS
KGLPQQLPAPPDEDDSAAPSTLSLLGPTFPGLSSCSA
DLKDILSEASTMQLLQQQQQEAVSEGSSSGRARERS
GAPTSSKDNYLGGTSTISDNAKELCKAVSVSMGLGV
EALEHLSPGEQLRGDCMYAPLLGVPPAVRPTPCAPLA
ECKGSLLDDSAGKSTEDTAEYSPFKGGYTKGLEGES
LGCSGSAAAGSSGTLELPSTLSLYKSGALDEAAAYQS
RDYYNFPLALAGPPPPPPPPHPHARIKLENPLDYGSA
WAAAAAQCRYGDLASLHGAGAAGPGSGSPSAAASS
SWHTLFTAEEGQLYGPCGGGGGGGGGGGGGGGG
GGGGGGGEAGAVAPYGYTRPPQGLAGQESDFTAPD
VWYPGGMVSRVPYPSPTCVKSEMGPWMDSYSGPY
GDMRLETARDHVLPIDYYFPPQKTCLICGDEASGCHY
GALTCGSCKVFFKRAAEGKQKYLCASRNDCTIDKFR
RKNCPSCRLRKCYEAGMTLGARKLKKLGNLKLQEEG
EASSTTSPTEETTQKLTVSHIEGYECQPIFLNVLEAIEP
GVVCAGHDNNQPDSFAALLSSLNELGERQLVHVVKW
AKALPGFRNLHVDDQMAVIQYSWMGLMVFAMGWRS
FTNVNSRMLYFAPDLVFNEYRMHKSRMYSQCVRMR
HLSQEFGWLQITPQEFLCMKALLLFSIIPVDGLKNQKF
FDELRMNYIKELDRIIACKRKNPTSCSRRFYQLTKLLD
SVQPIARELHQFTFDLLIKSHMVSVDFPEMMAEIISVQ
VPKILSGKVKPIYFHTQ (SEQ ID NO: 1)

FIG. 7

MEVQLGLGRVYPRPPSKTYRGAFQNLFQSVREVIQNP
GPRHPEAASAAPPGASLLLQQQQQQQQQQQQQQQQ
QQQQQQQQQQQQQETSPRQQQQQQGEDGSPQAHR
RGPTGYLVLDEEQQPSQPQSALECHPERGCVPEPGAA
VAASKGLPQQLPAPPDEDDSAAPSTLSLLGPTFPGLSS
CSADLKDILSEASTMQLLQQQQQEAVSEGSSSGRARE
ASGAPTSSKDNYLGGTSTISDNAKELCKAVSVSMGLGV
EALEHLSPGEQLRGDCMYAPLLGVPPAVRPTPCAPLAE
CKGSLLDDSAGKSTEDTAEYSPFKGGYTKGLEGESLG
CSGSAAAGSSGTLELPSTLSLYKSGALDEAAAYQSRDY
YNFPLALAGPPPPPPPPHPHARIKLENPLDYGSAWAAA
AAQCRYGDLASLHGAGAAGPGSGSPSAAASSSWHTL
FTAEEGQLYGPCGGGGGGGGGGGGGGGGGGGEAG
AVAPYGYTRPPQGLAGQESDFTAPDVWYPGGMVSRV
PYPSPTCVKSEMGPWMDSYSGPYGDMRLETARDHVL
PIDYYFPPQKTCLICGDEASGCHYGALTCGSCKVFFKR
AAEGKQKYLCASRNDCTIDKFRRKNCPSCRLRKCYEA
GMTLGEKFRVGNCKHLKMTRP      (SEQ ID NO: 2)

FIG. 8

MDPSGVKVLETAEDIQERRQQVLDRYHRFKELSTLRRQKLEDS
YRFQFFQRDAEELEKWIQEKLQIASDENYKDPTNLQGKLQKHQ
AFEAEVQANSGAIVKLDETGNLMISEGHFASETIRTRLMELHRQ
WELLLEKMREKGIKLLQAQKLVQYLRECEDVMDWINDKEAIVT
SEELGQDLEHVEVLQKKFEEFQTDMAAHEERVNEVNQFAAKLI
QEQHPEEELIKTKQDEVNAAWQRLKGLALQRQGKLFGAAEVQ
RFNRDVDETISWIKEKEQLMASDDFGRDLASVQALLRKHEGLE
RDLAALEDKVKALCAEADRLQQSHPLSATQIQVKREELITNWE
QIRTLAAERHARLNDSYRLQRFLADFRDLTSWVTEMKALINAD
ELASDVAGAEALLDRHQEHKGEIDAHEDSFKSADESGQALLAA
GHYASDEVREKLTVLSEERAALLELWELRRQQYEQCMDLQLF
YRDTEQVDNWMSKQEAFLLNEDLGDSLDSVEALLKKHEDFEK
SLSAQEEKITALDEFATKLIQNNHYAMEDVATRRDALLSRRNAL
HERAMRRRAQLADSFHLQQFFRDSDELKSWVNEKMKTATDEA
YKDPSNLQGKVQKHQAFEAELSANQSRIDALEKAGQKLIDVNH
YAKDEVAARMNEVISLWKKLLEATELKGIKLREANQQQQFNRN
VEDIELWLYEVEGHLASDDYGKDLTNVQNLQKKHALLEADVAA
HQDRIDGITIQARQFQDAGHFDAENIKKKQEALVARYEALKEPM
VARKQKLADSLRLQQLFRDVEDEETWIREKEPIAASTNRGKDLI
GVQNLLKKHQALQAEIAGHEPRIKAVTQKGNAMVEEGHFAAED
VKAKLHELNQKWEALKAKASQRRQDLEDSLQAQQYFADANEA
ESWMREKEPIVGSTDYGKDEDSAEALLKKHEALMSDLSAYGS
SIQALREQAQSCRQQVAPTDDETGKELVLALYDYQEKSPREVT
MKKGDILTLLNSTNKDWWKVEVNDRQGFVPAAYVKKLDPAQS
ASRENLLEEQGSIALRQEQIDNQTRITKEAGSVSLRMKQVEELY
HSLLELGEKRKGMLEKSCKKFMLFREANELQQWINEKEAALTS
EEVGADLEQVEVLQKKFDDFQKDLKANESRLKDINKVAEDLES
EGLMAEEVQAVQQQEVYGMMPRDETDSKTASPWKSARLMVH
TVATFNSIKELNERWRSLQQLAEERSQLLGSAHEVQRFHRDAD
ETKEWIEEKNQALNTDNYGHDLASVQALQRKHEGFERDLA

FIG. 8 (cont'd)

ALGDKVNSLGETAERLIQSHPESAEDLQEKCTELNQAWSSL
GKRADQRKAKLGDSHDLQRFLSDFRDLMSWINGIRGLVSSD
ELAKDVTGAEALLERHQEHRTEIDARAGTFQAFEQFGQQLL
AHGHYASPEIKQKLDILDQERADLEKAWVQRRMMLDQCLEL
QLFHRDCEQAENWMAAREAFLNTEDKGDSLDSVEALIKKHE
DFDKAINVQEEKIAALQAFADQLIAAGHYAKGDISSRRNEVLD
RWRRLKAQMIEKRSKLGESQTLQQFSRDVDEIEAWISEKLQ
TASDESYKDPTNIQSKHQKHQAFEAELHANADRIRGVIDMGN
SLIERGACAGSEDAVKARLAALADQWQFLVQKSAEKSQKLK
EANKQQNFNTGIKDFDFWLSEVEALLASEDYGKDLASVNNL
LKKHQLLEADISAHEDRLKDLNSQADSLMTSSAFDTSQVKDK
RDTINGRFQKIKSMAASRRAKLNESHRLHQFFRDMDDEESW
IKEKKLLVGSEDYGRDLTGVQNLRKKHKRLEAELAAHEPAIQ
GVLDTGKKLSDDNTIGKEEIQQRLAQFVEHWKELKQLAAAR
GQRLEESLEYQQFVANVEEEEAWINEKMTLVASEDYGDTLA
AIQGLLKKHEAFETDFTVHKDRVNDVCTNGQDLIKKNNHHEE
NISSKMKGLNGKVSDLEKAAAQRKAKLDENSAFLQFNWKAD
WESWIGEKENSLKTDDYGRDLSSVQTLLTKQETFDAGLQAF
QQEGIANITALKDQLLAAKHVQSKAIEARHASLMKRWSQLLA
NSAARKKKLLEAQSHFRKVEDLFLTFAKKASAFNSWFENAEE
DLTDPVRCNSLEEIKALREAHDAFRSSLSSAQADFNQLAELD
RQIKSFRVASNPYTWFTMEALEETWRNLQKIIKERELELQKE
QRRQEENDKLRQEFAQHANAFHQWIQETRTYLLDGSCMVE
ESGTLESQLEATKRKHQEIRAMRSQLKKIEDLGAAMEEALILD
NKYTEHSTVGLAQQWDQLDQLGMRMQHNLEQQIQARNTT
GVTEEALKEFSMMFKHFDKDKSGRLNHQEFKSCLRSLGYDL
PMVEEGEPDPEFEAILDTVDPNRDGHVSLQEYMAFMISRET
ENVKSSEEIESAFRALSSEGKPYVTKEELYQNLTREQADYCV
SHMKPYVDGKGRELPTAFDYVEFTRSLFVN (SEQ ID NO: 3)

FIG. 9

MAESSDKLYRVEYAKSGRASCKKCSESIPKDSLRMAIMVQSP
MFDGKVPHWYHFSCFWKVGHSIRHPDVEVDGFSELRWDDQ
QKVKKTAEAGGVTGKGQDGIGSKAEKTLGDFAAEYAKSNRST
CKGCMEKIEKGQVRLSKKMVDPEKPQLGMIDRWYHPGCFVK
NREELGFRPEYSASQLKGFSLLATEDKEALKKQLPGVKSEGK
RKGDEVDGVDEVAKKKSKKEKDKDSKLEKALKAQNDLIWNIK
DELKKVCSTNDLKELLIFNKQQVPSGESAILDRVADGMVFGAL
LPCEECSGQLVFKSDAYYCTGDVTAWTKCMVKTQTPNRKEW
VTPKEFREISYLKKLKVKKQDRIFPPETSASVAATPPPSTASAP
AAVNSSASADKPLSNMKILTLGKLSRNKDEVKAMIEKLGGKLT
GTANKASLCISTKKEVEKMNKKMEEVKEANIRVVSEDFLQDV
SASTKSLQELFLAHILSPWGAEVKAEPVEVVAPRGKSGAALS
KKSKGQVKEEGINKSEKRMKLTLKGGAAVDPDSGLEHSAHVL
EKGGKVFSATLGLVDIVKGTNSYYKLQLLEDDKENRYWIFRS
WGRVGTVIGSNKLEQMPSKEDAIEHFMKLYEEKTGNAWHSK
NFTKYPKKFYPLEIDYGQDEEAVKKLTVNPGTKSKLPKPVQDL
IKMIFDVESMKKAMVEYEIDLQKMPLGKLSKRQIQAAYSILSEV
QQAVSQGSSDSQILDLSNRFYTLIPHDFGMKKPPLLNNADSV
QAKVEMLDNLLDIEVAYSLLRGGSDDSSKDPIDVNYEKLKTDI
KVVDRDSEEAEIIRKYVKNTHATTHNAYDLEVIDIFKIEREGEC
QRYKPFKQLHNRRLLWHGSRTTNFAGILSQGLRIAPPEAPVT
GYMFGKGIYFADMVSKSANYCHTSQGDPIGLILLGEVALGNM
YELKHASHISKLPKGKHSVKGLGKTTPDPSANISLDGVDVPLG
TGISSGVNDTSLLYNEYIVYDIAQVNLKYLLKLKFNFKTSLW (SEQ ID NO: 4)

TREATMENTS AND DIAGNOSTICS FOR CANCERS

CROSS-REFERENCE TO RELATED APPLICATIONS

This application is the U.S. National Phase of International Application No. PCT/US2016/057210, filed Oct. 14, 2016, which claims priority to U.S. Provisional Patent Application No. 62/241,574 filed Oct. 14, 2015, and U.S. Provisional Patent Application No. 62/259,426 filed Nov. 24, 2015, each of which are incorporated herein by reference in their entirety as if fully set forth herein.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 15-1330 Seq Listing_ST25.txt. The text file is about 7 KB, was created on Mar. 9, 2018, and is being submitted electronically via EFS-Web.

FIELD OF THE DISCLOSURE

The present disclosure provides treatments and diagnostics for cancers. The treatments utilize a combination therapy of Galeterone and a proteasome inhibitor. The diagnostics can measure androgen receptor (AR) cleavage products including AR-variant 7 (AR-V7) cleavage products, Poly (ADP-ribose) polymerase (PARP) cleavage products, and/or Spectrin α2 cleavage products or inhibition of DUB activities from a blood sample to monitor treatment efficacy for castration-resistant prostate cancer (CRPC) or multiple myeloma (MM).

BACKGROUND OF THE DISCLOSURE

Cancer (neoplasia) is characterized by deregulated cell growth and cell division. There are numerous types of cancers. As one example, prostate cancer, as its name indicates, is a cancer that develops in the prostate gland of the male reproductive system. Prostate cancer can be aggressive, in which cancer cells metastasize and move from the prostate gland to other parts of the body, such as the lymph nodes and the bones. It is the second leading cause of cancer-related death in men in the US, and its prevalence is increasing in developing countries.

More than 200,000 new cases of prostate cancer are diagnosed in the US each year. Of these, roughly 88% or 176,000 have localized disease that can be treated with surgery, radiation, cryotherapy or watchful waiting.

Prostate cancer growth is often driven by male sex hormones called androgens, which include testosterone. Because of this, a common treatment option for the 22% or 35,200 patients that cannot be treated with surgery, radiation, cryotherapy or watchful waiting is to lower the levels of androgens in the man's body. Androgen levels can be lowered by surgically removing the testicles or with drugs that stop the testicles, and to a lesser extent adrenal glands, from making androgens or block how they affect the body. This type of treatment is called hormone therapy or androgen-deprivation therapy.

Unfortunately, about 40,000 patients each year begin to fail hormone therapy or become hormone refractory. That is, they develop castration-resistant prostate cancer (CRPC) or hormone refractory prostate cancer (HRPC).

Treatment options for prostate cancer are very limited once the disease becomes resistant to hormonal therapy. In the past few years, docetaxel was the only treatment option for patients with CRPC.

Recently, the FDA approved a chemotherapeutic drug, cabazitaxel, for clinical management of CRPC. Cabazitaxel has shown survival benefits for patients with CRPC. The drug is used to treat men with advanced prostate cancer after treatment with other anticancer agents, including docetaxel, have failed to curtail cancer progression. Thus, cabazitaxel is mostly administered to patients when docetaxel is no longer effective.

Although cabazitaxel has been shown to increase the overall survival of prostate cancer patients, it has serious adverse side effects. These include low white blood cell count, low red blood cell count, low blood platelet count, nausea, vomiting, constipation and diarrhea, and decreased appetite, shortness of breath, tiredness and hair loss.

Galeterone also named TOK-001 or VN/124-1, is a small molecule, oral drug that is capable of disrupting androgen receptor signaling. In preclinical studies, Galeterone has been shown to selectively inhibit cytochrome $C_{17}\alpha$-hydroxylase/$C_{17}$-20-lyase (CYP17) lyase to prevent biosynthesis of androgens, antagonize testosterone binding to the androgen receptor (AR), and degrade the AR protein. Galeterone is the first drug in development that has been shown to have all three properties. At the time of this application's filing, Galeterone is undergoing a Phase III clinical trial for the treatment of metastatic CRPC.

SUMMARY OF THE DISCLOSURE

The current disclosure provides compositions and methods to potentiate treatment with Galeterone for a variety of cancers. The compositions and methods utilize administration of proteasome inhibitors, which, as disclosed herein, can be used to potentiate the beneficial anti-cancer effects of Galeterone and/or to reduce toxicity (e.g., lower the required dose) of administered Galeterone. Without being bound by theory, administration of proteasome inhibitors sensitizes cancer cells to the beneficial anti-cancer effects of Galeterone.

The current disclosure also provides systems and methods to monitor anti-cancer effects of CRPC treatments (e.g., Galeterone administration) by measuring blood levels of cleavage products of androgen receptor (AR), Poly (ADP-ribose) polymerase (PARP), and/or Spectrin α2, and more particularly, in particular embodiments, AR-variant 7 (AR-V7) cleavage products including 53 kDa and 41 kDa AR-V7 fragments, PARP cleavage products including 89 kDa and 65 kDa PARP fragments, and Spectrin α2 cleavage products including 120 kDa and 150 kDa Spectrin α2 fragments.

without or with 50 µM of the calpain inhibitor ALLM or a pan-caspase inhibitor for up to 72 h. This was followed by Western blotting with specific AR-V7 antibody, with Actin as a loading control.

Figure 2A:
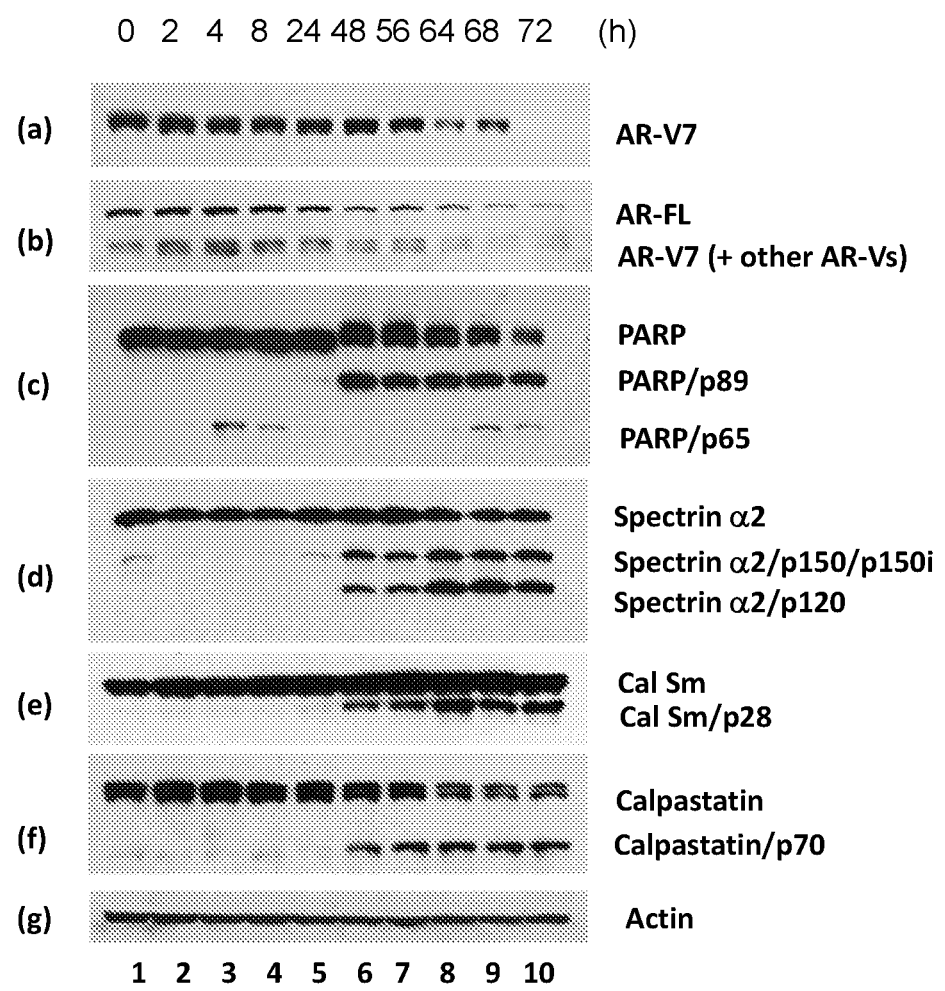
Figure 2B:
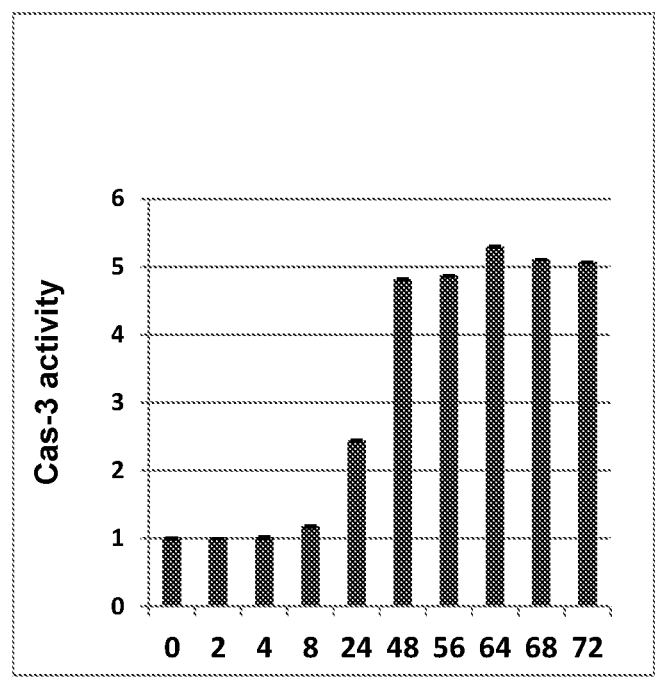

FIGS. 2A and 2B: Gal induces activation of caspase-3 and calpain followed by AR-V7 degradation. 22Rv1 cells were treated with 20 µM Gal for up to 72 h. FIG. 2A. Western blotting. (a, b) AR-V7 and AR protein levels determined by AR-V7 specific antibody and N20 antibody, respectively. (c) PARP/p89 is a caspase-3 cleavage fragment while PARP/p65 is a calpain cleavage product. (d) Caspase-3 cleavage fragment of Spectrin α2/p120, and a 150 fragment by either caspase-3 or calpain cleavage. (e) Autolysis of calpain small subunit (Cal Sm) to p28 fragment. (f) Calpain cleavage fragment of Calpastatin/p70. FIG. 2B. Caspase-3 activity assay.

Figure 3A:
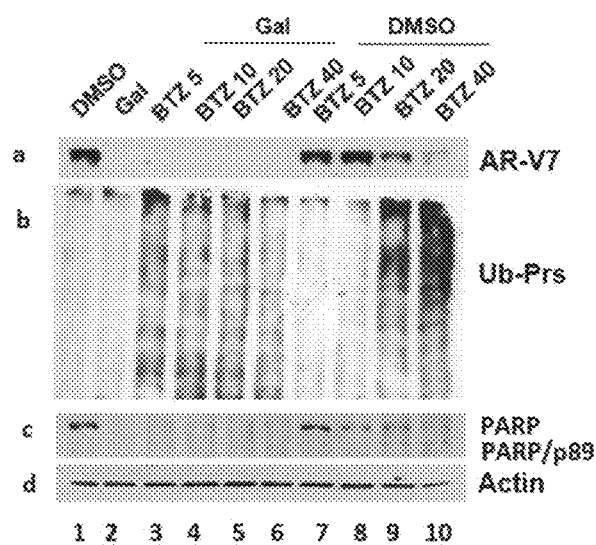
Figure 3B:
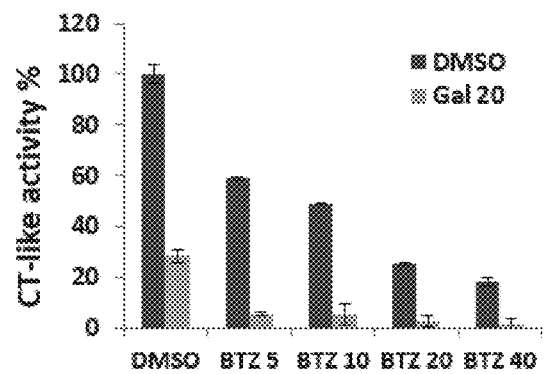
Figure 3C:
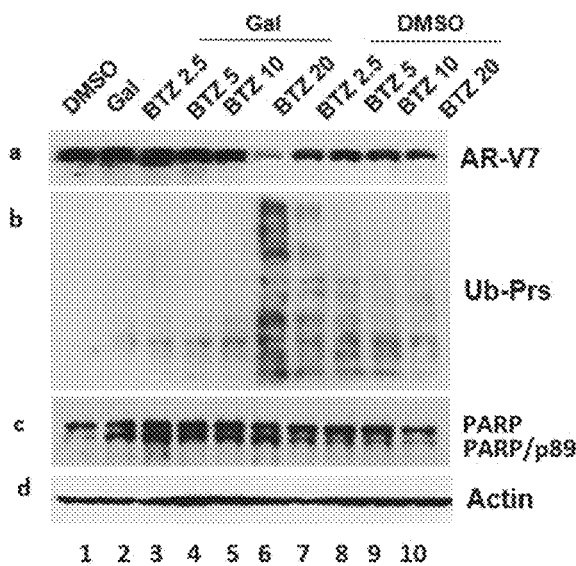
Figure 3D:
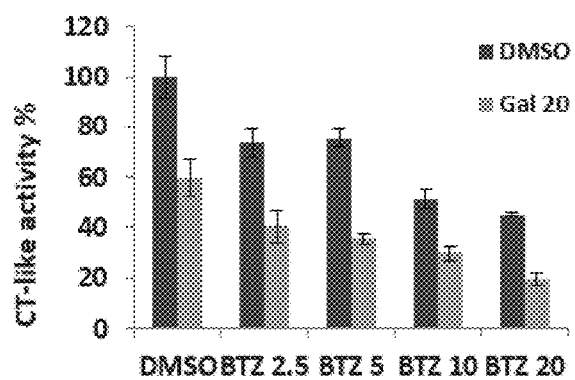

FIGS. 3A-3D: Proteasome Inhibition could not block, instead increase Gal-Induced AR-V7 degradation and PARP cleavage. 22Rv1 cells were treated with 20 µM Gal with or without BTZ at indicated concentrations (DMSO as a control) for 72 h (FIG. 3A, 3B) or 48 h (FIG. 3C, 3D), followed by Western blotting with specific AR-V7 mAb and PARP (FIG. 3A, 3C) and proteasome activity (FIG. 3B, 3D).

FIGS. 4A-4D: Gal inhibits the proteasomal activities in CRPC cells. 22Rv1 cells were treated with 5-20 µM Gal for 24 h (FIG. 4A) or 48 h (FIG. 4B), or VCaP cells treated with 5-20 µM Gal for 72 h (FIG. 4C), with 100 nM BTZ as a control, followed by assaying proteasomal CT-like, PGPH-like, and T-like activities. (FIG. 4D) 22Rv1 cells were treated with 20 µM Gal for up to 72 h, followed by assaying CT-like activity.

Figure 5A:
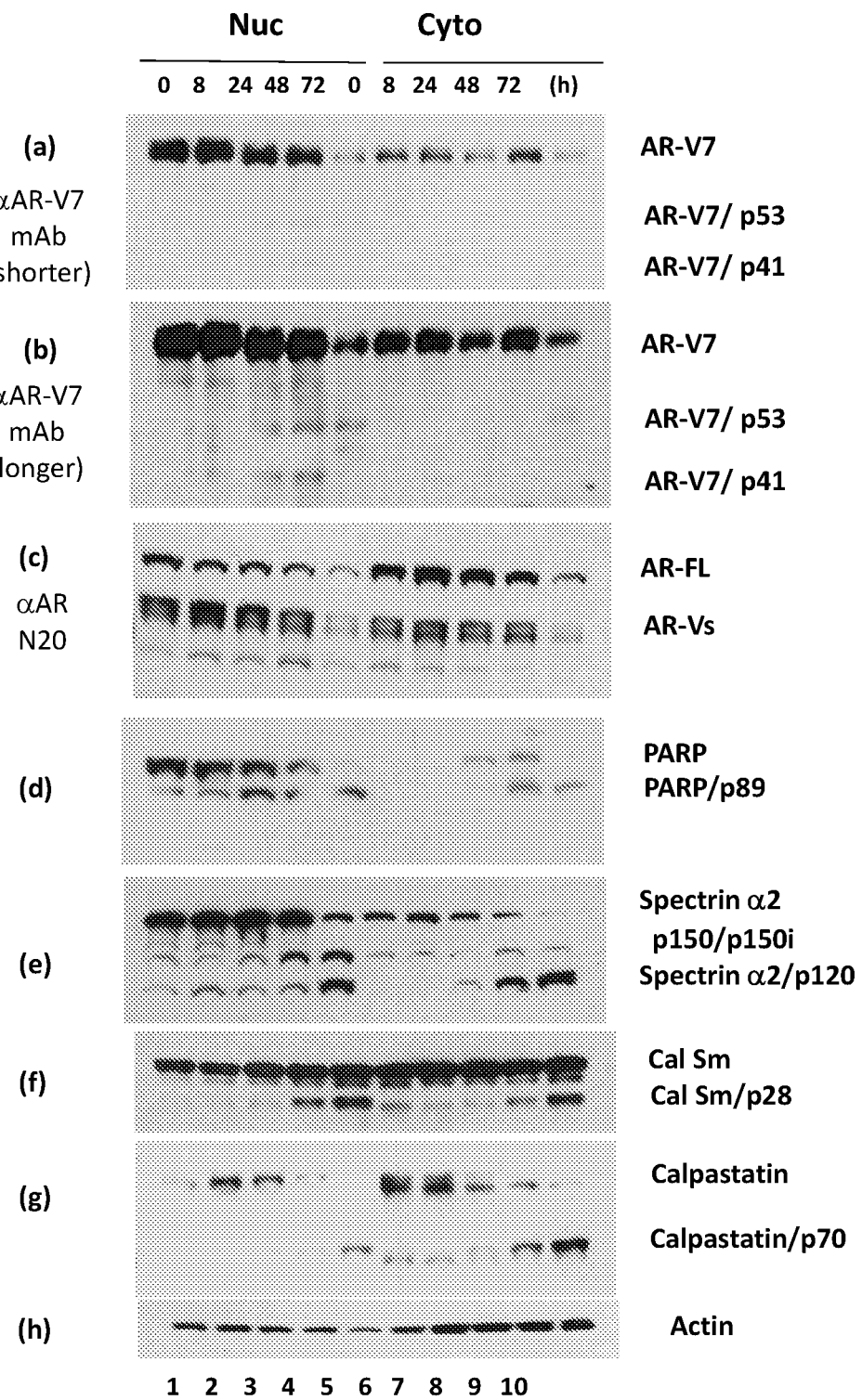

FIGS. 5A-5D: FIG. 5A—Cellular localizations of AR and AR-V7 as well as calpain/caspase substrate proteins and their cleavage fragments in Gal-treated R22v1. 22Rv1 cells were treated with 20 µM Gal for up to 72 h, followed by isolating nuclear (Nuc) and cytosolic (Cyto) fractions and analysis in Western blotting (35 µg/lane) using below antibodies: (a, b) Anti-AR-V7 monoclonal antibody, shorter and longer exposures, respectively; (c) Anti-AR (N20); (d) Anti-PARP; (e) Anti-Spectrin α2; (f) Anti-calpain small subunit; (g) Anti-Calpastatin; (h) Anti-actin. (FIG. 5B-D) Nuclear AR-V7 cleavage fragment(s) and effects of calpain/caspase inhibitors in Gal-treated 22Rv1 cells. B, Cleavage of AR-V7 in nuclei. 22 Rv1 cells, with androgen starvation for 24 h, were treated with 20 µM of Gal for indicated hours, followed by isolation of nuclear (Nu) and cytosolic (Cyto) fractions and Western blotting with specific antibodies indicated. The 53 kDa fragment was detected by the AR-V7-specific monoclonal antibody. (C, D) Inhibitors of calpain and caspases block the nuclear AR-V7 degradation in Gal-treated CRPC cells. 22 Rv1 cells, without (C) or with androgen starvation for 24 h (D), were treated with 20 µM of Gal in the absence or presence of 40 µM of calpain inhibit calpeptin (CAPT) (C, D), 40 µM of pan-caspase inhibitor IV (Cas IV) (C), or 20 µM of caspase inhibitor Z-VAD (D) for different time points. Nuclear fractions were isolated and separated by Western blotting to determine AR-V7 levels. Actin was used as a loading control.

FIG. 6 provides an exemplary human AR sequence (SEQ ID NO: 1).

FIG. 7 provides an exemplary human AR variant sequence (SEQ ID NO: 2) (ref. 66).

FIG. 8 provides an exemplary human Spectrin α2 sequence (SEQ ID NO: 3).

FIG. 9 provides an exemplary human PARP sequence (SEQ ID NO: 4).

FIGS. 10A-10E. Gal inhibits 19S proteasome-associated DUB, but not 20S proteasomal catalytic activities. Purified 20S proteasome (FIG. 10A), purified 26S proteasome (FIG. 10B), or protein extract of 22Rv1 cells (FIG. 10C) was incubated with Gal (µM) or BTZ (nM) at indicated concentrations for 15 min, and the proteasome activities were determined. (FIG. 10D and FIG. 10E) Purified 26S proteasome was incubated with Gal (20 µM or as indicated) for 15 min, and then Ub-AMC substrate was added to determine DUBs activity. Purified 20S proteasome was used a control; BG, background (10D).

Figure 11A:
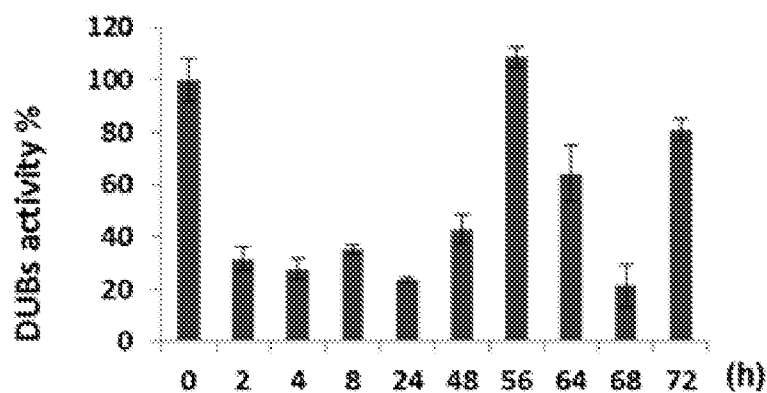
Figure 11B:
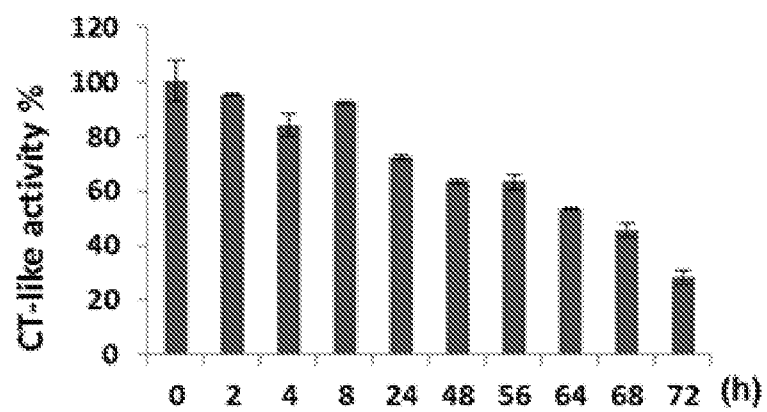
Figure 11C:
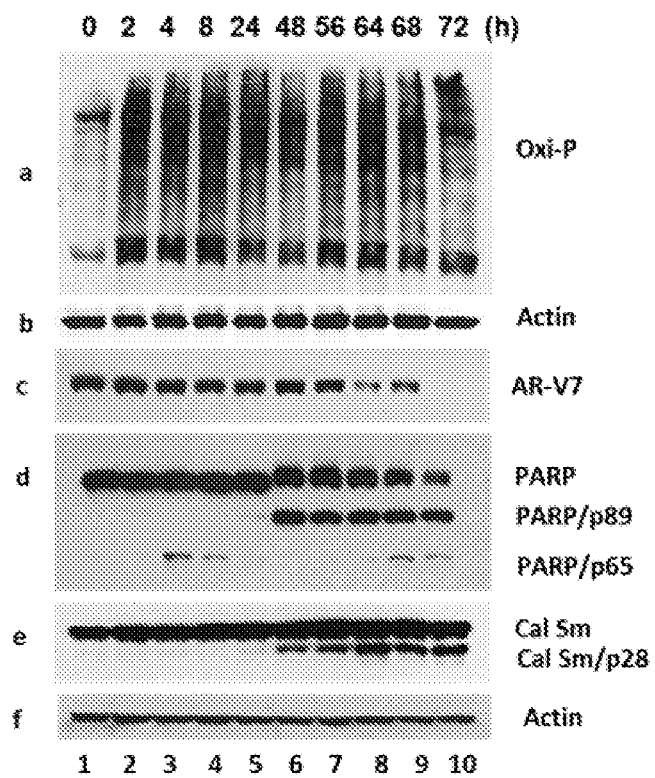
Figure 11D:
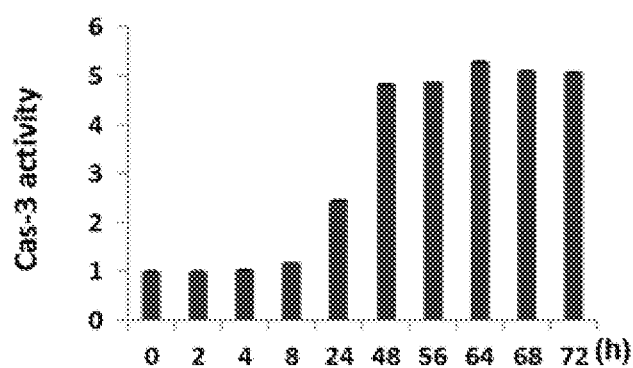

FIGS. 11A-11D. Gal induces DUB inhibition and protein oxidization in castrate-resistant prostate cancer cells. 22Rv1 cells were treated with 20 µM galeterone (Gal) for up to 72 h, followed by measuring levels of DUB activity (FIG. 11A), proteasomal CT-like activity (FIG. 11B), Western blotting (FIG. 11C) and caspase-3 activity (FIG. 11D). In C, (a) Cell lysates were derivatized with 2,4-dinitrophenylhydrazine (DNPH), followed by Western blotting to determine the levels of oxidized proteins (Oxi-P). Actin was used a load control (b). AR-V7 levels were determined by AR-V7 specific antibody (c). PARP/p89 is caspase-3 cleavage fragment while PARP/p65 is calpain cleavage product (d). (e) Autolysis of calpain small subunit (Cal Sm) to p28 fragment. (f) Actin, loading control.

FIGS. 12A-E. Gal and BTZ combination induced greater levels of growth inhibition and cell death in CRPC cells. (FIG. 12A) 22Rv1 cells were treated with Gal at indicated concentrations in the presence of different concentrations of bortezomib (BTZ) for 24 h, cell proliferation was determined by MTT. (FIG. 12B-C) Morphological changes after bortezomib and Gal combination treatment for 24 h. 22Rv1 cells were treated with Gal (20 µM) in the presence of indicated concentrations (nM) of bortezomib (BTZ) for 24 h, morphological changes (12B) and crystal violet staining (12C) were determined. In 12C, cells were fixed with formalin, and then stained with violet overnight. (FIG. 12D-E) 22Rv1 cells were treated with Gal (20 µM) in the presence of indicated concentrations (nM) of bortezomib (BTZ) for 48 h, morphological changes (12D) and crystal violet staining (12E) were determined.

Figure 13A:
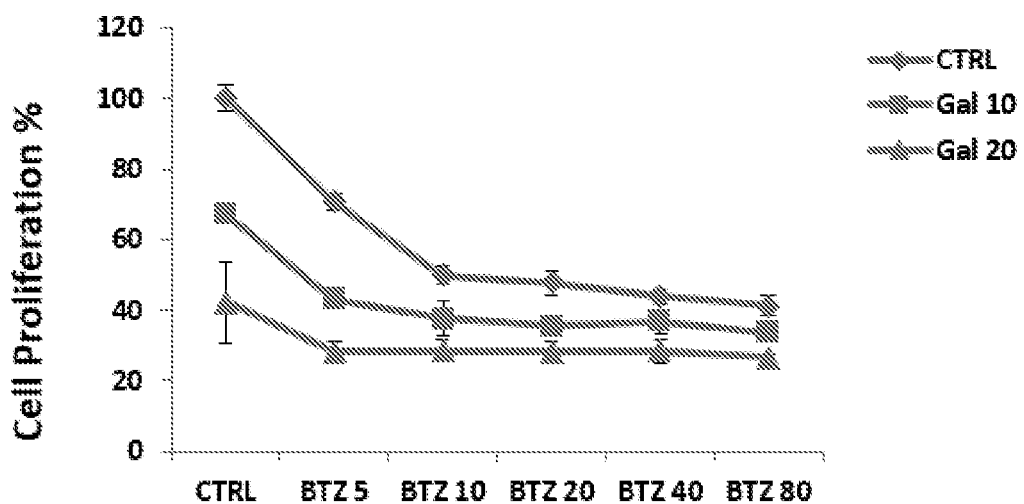
Figure 13B:
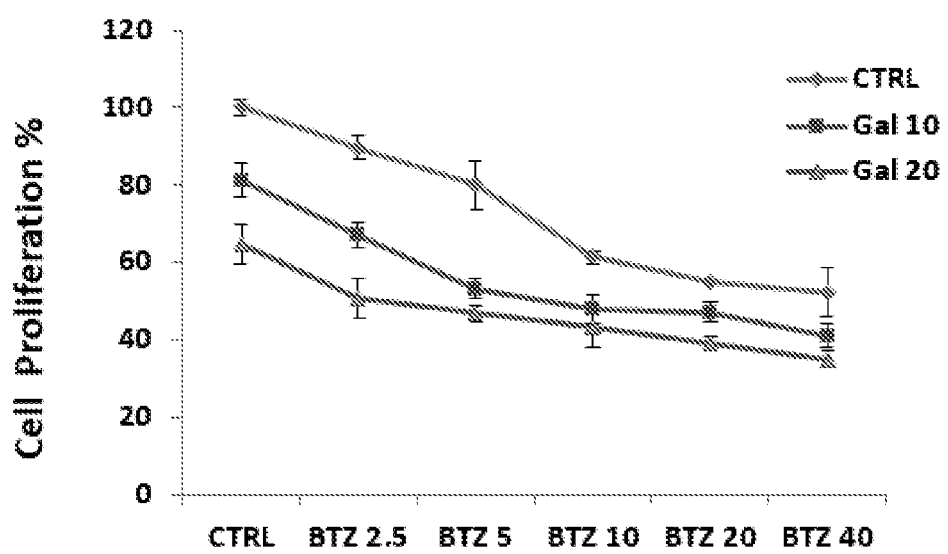
Figure 13C:
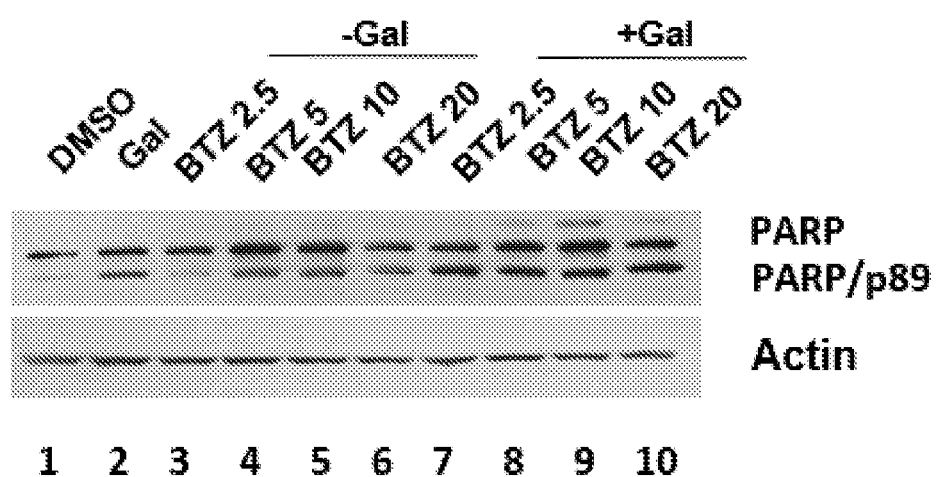

FIGS. 13A-C. Gal overcomes BTZ resistance in MM. BTZ-resistant MM 8826 cells were treated with Gal (10-20 µM) in combination with BTZ (2.5-40 nM) for 24 h (FIG. 13A, FIG. 13B from two independent experiments). Cell proliferation was determined by MTS. (FIG. 13C) Multiple myeloma 8826 cells were treated with 0.5-4 nM bortezomib (BTZ) in the presence of 10 µM of Gal for 24 h. Cell death was determined by detection of PARP cleavage. Increased levels of PARP cleavage were seen in the combination treated cells. Actin was used as loading control.

DETAILED DESCRIPTION

Cancer (neoplasia) is characterized by deregulated cell growth and cell division. There are numerous types of cancers. Examples of cancers include acoustic neuroma, adenocarcinoma, astrocytoma, basal cell cancer, bile duct cancer, bladder cancer, brain cancer, breast cancer, bronchogenic cancer, central nervous system cancer, cervical cancer, chondrosarcoma, choriocarcinoma, chronic lymphocytic leukemia, colon cancer, craniopharyogioma, ependymoma, Ewing's tumor, fibrosarcoma, glandular cancer, glioma, hairy cell leukemia, hemangioblastoma, hepatocellular carcinoma, hepatoma, kidney cancer, leiomyosarcoma, liver cancer, liposarcoma, lung cancer, melanoma, medulloblastoma, medullary cancer, medullary thyroid cancer, menangioma, mesothelioma, multiple myeloma (MM), myxosarcoma, neuroblastoma, non-Hodgkin's lymphoma, oligodendroglioma, osteogenic sarcoma, ovarian cancer, papillary adenocarcinomas, papillary thyroid cancer, pancreatic cancer, pheochromocytomas papillary cancer, pineal cancer, prolymphocytic leukemia, prostate cancer (including castration-resistant prostate cancer), renal cell cancer, retinoblastoma, rhabdomyosarcoma, sarcoma, sebaceous gland cancer, seminoma, skin cancer, squamous cell cancer, sweat gland cancer, synoviona, testicular cancer, and/or Wilms' tumor.

As one example, multiple myeloma (MM) is a cancer of plasma cells, a type of white blood cell normally responsible for producing antibodies. In multiple myeloma, collections of abnormal plasma cells accumulate in the bone marrow, where they interfere with the production of normal blood cells. Most cases of multiple myeloma also feature the production of a paraprotein—an abnormal antibody which can cause kidney problems. Bone lesions and hypercalcemia (high blood calcium levels) are also often encountered. Multiple myeloma is considered to be incurable but treatable. Remissions may be induced with steroids, chemotherapy, proteasome inhibitors, immunomodulatory drugs such as thalidomide or lenalidomide, and stem cell transplants. Radiation therapy is sometimes used to reduce pain from bone lesions.

Another example of a cancer is prostate cancer. Prostate cancer, as its name indicates, is a cancer that develops in the prostate gland of the male reproductive system. Prostate cancer can be aggressive, in which cancer cells metastasize and move from the prostate gland to other parts of the body, such as the lymph nodes and the bones. It is the second leading cause of cancer-related death in men in the US, and its prevalence is increasing in developing countries.

More than 200,000 new cases of prostate cancer are diagnosed in the US each year. Of these, roughly 88% or 176,000 have localized disease that can be treated with surgery, radiation, cryotherapy or watchful waiting.

Prostate cancer growth is often driven by male sex hormones called androgens, which include testosterone. Because of this, a common treatment option for the 22% or 35,200 patients that cannot be treated with surgery, radiation, cryotherapy or watchful waiting is to lower the levels of androgens in the man's body. Androgen levels can be lowered by surgically removing the testicles or with drugs that stop the testicles from making androgens or block how they affect the body. This type of treatment is called hormone therapy or androgen-deprivation therapy.

Unfortunately, about 40,000 patients each year begin to fail hormone therapy or become hormone refractory. That is, they develop castration-resistant prostate cancer (CRPC) or hormone refractory prostate cancer (HRPC). CRPC is particularly prostate cancer that continues to grow despite the suppression of male hormones that fuel the growth of prostate cancer cells.

Androgen receptors (AR), also known as NR3C4 (nuclear receptor subfamily 3, group C, member 4), are a type of nuclear receptor that are activated by binding either of the androgenic hormones, testosterone, or dihydrotestosterone in the cytoplasm. Upon binding, AR translocates into the cell nucleus. The AR is most closely related to the progesterone receptor, and progestins in higher dosages can block AR.

The AR contains a N-terminal domain (NTD), a DNA binding domain (DBD), a hinge region (H) and a C-terminal domain (CTD). The CTD contains the Ligand Binding Domain (LBD) and the Transcriptional Activation Function 2 Domain (AF2). Androgen Receptor Variants (ARVs) lack the LBD and are constituently active in the absence of ligand (AR-V3, AR-V4, AR-V5, AR-V7 and AR-V12). A human AR sequence can be found at, for example, Accession: AAA51772.1 and this sequence is provided in FIG. 6. A human variant AR sequence can be found at Accession: ACN39559.1 and this sequence is provided in FIG. 7.

Among the contributors to CRPC are AR splice variants that lack the LBD. Instead, AR splice variants have small amounts of unique sequences derived from cryptic exons or from out of frame translation. Androgen Receptor Variant 7 (AR-V7) is constitutively active and is expressed under conditions consistent with CRPC. AR-V7 is reported to regulate a transcriptional program that is similar but not identical to that of AR. However, it is unknown whether these differences are due to the unique sequences in AR-V7, or simply to loss of the LBD.

Galeterone, also named TOK-001 and VN/124-1, is a small molecule, oral drug that is capable of disrupting androgen receptor signaling. In preclinical studies, Galeterone has been shown to selectively inhibit CYP17 lyase to prevent biosynthesis of androgens, antagonize testosterone binding to the androgen receptor (AR), and degrade the AR protein. Galeterone is the first drug in development that has been shown to have all three properties. At the time of this application's filing, Galeterone is undergoing a Phase III clinical trial for the treatment of metastatic CRPC.

Galeterone has been shown to be effective against the full length AR (fAR) and AR-V7, causing tumor regression in preclinical models. Activities are shown by reductions in Prostate-specific antigen (PSA), Transmembrane protease, serine 2 (TMPRSS2) and Homeobox protein Nkx-3.1 (NKX3.1).

Particular embodiments of Galeterone have a molecular formula of $C_{26}H_{32}N_2O$ and a molecular weight of about 388.55 g/mol. Particular embodiments of Galeterone include (3S,8R,9S,10R,13S,14S)-17-(benzimidazol-1-yl)-10,13-dimethyl-2,3,4,7,8,9,11,12,14,15-decahydro-1H-cyclopenta[a]phenanthren-3-ol. Particular embodiments of Galeterone include 3-β-Hydroxy17-(1H-benzimidazol-1-yl)androsta-5,16-diene).

Particular embodiments of Galeterone include compounds of formula (I)

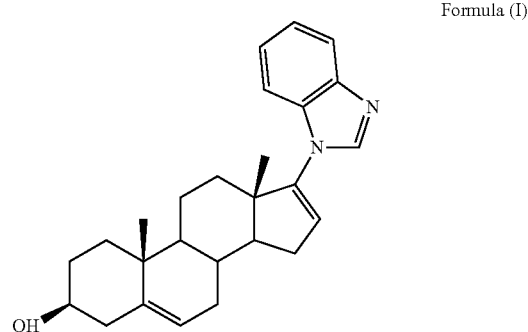 [SMILES: C[C@]12CC[C@H](O)CC1=CCC1C2CC[C@]2(C)C(n3cnc4ccccc43)=CCC12]

Formula (I)

Particular embodiments of Galeterone include analogs which include pharmaceutically acceptable salts, N-oxides, active metabolites, prodrugs, or solvates of Formula 1.

Particular embodiments of Galeterone include analogs which include compounds of formula (II) or a pharmaceutically acceptable salt, N-oxide, active metabolite, prodrug, or solvate thereof

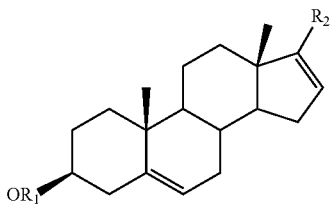

Formula (II)

wherein R$_1$ is H or acetyl; and R$_2$ is pyridyl or benzimidazolyl. Additional embodiments of Galeterone analogs are disclosed in US 2014/0288037.

The current disclosure provides compositions and methods to potentiate the anti-cancer effects of Galeterone. Potentiating the anti-cancer effects of Galeterone means that at least one anti-cancer effect of Galeterone is increased, and in particular embodiments is statistically-significantly increased. The potentiation can be used to increase the anti-cancer effect of Galeterone, or, in particular embodiments, to lower the required dose of Galeterone to reduce potential side effects or toxicities of drug administration or allow for more Galeterone to be tolerated for greater drug concentration and subsequently greater efficacy.

The compositions and methods that potentiate the anti-cancer effects of Galeterone utilize administration of proteasome inhibitors in combination with Galeterone. Without being bound by theory, administration of proteasome inhibitors sensitizes cancer cells to the beneficial anti-cancer effects of Galeterone because Galeterone itself is a proteasome inhibitor. Galeterone also inhibits deubiquitinating enzymes (DUBs).

The 19S proteasome subunit (PA700/19S) plays essential roles in processing ubiquitylated substrates; it can bind, deubiquitylate, and unfold ubiquitylated proteins, which then translocate into the proteolytic chamber of the 20S proteasome for degradation. The 20S proteasome subunit (20S) is a 700-kDa proteasome that has multiple peptidase activities that function through a new type of proteolytic mechanism involving a threonine active site. The 26S proteasome degrades ubiquitylated proteins. It includes the 20S proteasome and the PA700/19S complex.

Deubiquitinating enzymes (DUBs) are also known as deubiquitinating peptidases, deubiquitinating isopeptidases, deubiquitinases, ubiquitin proteases, ubiquitin hydrolases, and ubiquitin isopeptidases. DUBs are a large group of proteases that cleave ubiquitin from proteins and other molecules. Ubiquitin is attached to proteins in order to regulate the degradation of proteins via the proteasome and lysosome; coordinate the cellular localization of proteins; activate and inactivate proteins; and modulate protein-protein interactions. DUBs can reverse these effects by cleaving the peptide or isopeptide bond between ubiquitin and its substrate protein. In humans there are nearly 100 DUB genes, which can be classified into two main classes: cysteine proteases and metalloproteases. The cysteine proteases include ubiquitin-specific proteases (USPs), ubiquitin C-terminal hydrolases (UCHs), Machado-Josephin domain proteases (MJDs) and ovarian tumor proteases (OTU). The metalloprotease group includes the Jab1/Mov34/Mpr1 Pad1 N-terminal+ (MPN+) (JAMM) domain proteases.

Proteasome inhibitors are molecules that block the activity of proteasomes, which are proteolytic complexes that degrade cytosolic and nuclear proteins into small peptide units. Examples of proteasome inhibitors include lactacystin, bortezomib, disulfiram, epigallocatechin-3-gallate, salinosporamide A, carfilzomib, oprozomib (ONX 0912), CEP-18770, laxomib (MLN9708), epoxomicin, β-lapachone, and MG132. Bortezomib is a first-generation proteasome inhibitor. Examples of second-generation proteasome inhibitors include MLN9708, CEP-18770, carfilzomib, salinosporamide A (NPI-0052, marizomib), oprozomib (ONX 0912) and immunoproteasome inhibitors (e.g., UK-101, IPSI-001, YU-102, ONX 0914, PR-924 (IPSO). Bortezomib has been approved in the US for the treatment of multiple myeloma. Moreover, proteasomal inhibitors such as Brotezamide, MG132, and β-lapachone inhibit the 20S proteasome. Therefore, these drugs inhibit the entire proteasomal activity including the 26S (which includes the 20S and 19S) and the 20S proteasomal complexes.

In particular embodiments, cancer cells (e.g., CRPC cells, MM cells) are sensitized to the beneficial anti-cancer effects of Galeterone due to activation of calpains/caspases. For example, in CRPC cells, calpains/caspases cleave AR and the variant AR (e.g., AR-V7), resulting in cancer cell death.

Calpains belong to a family of calcium-dependent, non-lysosomal cysteine proteases (proteolytic enzymes) expressed ubiquitously in mammals and many other organisms. Amongst protein substrates, tertiary structure elements rather than primary amino acid sequences are likely responsible for directing cleavage to a specific substrate. Amongst peptide and small-molecule substrates, the most consistently reported specificity is for small, hydrophobic amino acids (e.g. leucine, valine and isoleucine) at the P2 position, and large hydrophobic amino acids (e.g. phenylalanine and tyrosine) at the P1 position. Calpains have been implicated in necrotic and apoptotic cell death.

The calpain family includes two major isoforms, calpain I and calpain II which require μM and mM $Ca^{2+}$ concentrations to initiate activity. An increase in intracellular $Ca^{2+}$ level is thought to trigger a cascade of biochemical processes including calpain activation. Once activated, calpains degrade membrane, cytoplasmic and nuclear substrates, leading to the breakdown of cellular architecture and finally apoptosis.

Like calpains, caspases are cysteine proteases. Caspases are a family of cysteine aspartic proteases or cysteine-dependent aspartate-directed proteases that play an important role in apoptosis, necrosis, and inflammation. Caspases are essential in cellular processes including apoptosis, in development and in stages of adult life. Some caspases are also required in the immune system for the maturation of lymphocytes. Failure of apoptosis has been shown to contribute to tumor development, chemoresistance and autoimmune diseases. It has been shown that caspases and calpains interact with each other to increase or decrease apoptosis.

There are two types of apoptotic caspases, the initiator (apical) caspases and the effector (executioner) caspases. The initiator caspases cleave inactive pro-forms of effector caspases, thereby activating them. The effector caspases subsequently cleave other protein substrates within the cell to trigger the apoptotic process. The initiation of this caspase cascade is regulated by caspase inhibitors.

Examples of initiator caspases include Caspase-2 (CASP2), Caspase-8 (CASP8), Caspase-9 (CASP9), and Caspase-10 (CASP10). Examples of effector caspases include Caspase-3 (CASP3), Caspase-6 (CASP6), and Caspase-7 (CASP7). Other caspases that are not classified as an initiator or effector caspases include Caspase-4 (CASP4), Caspase-5 (CASP5), and Caspase-1 (CASP1). CASP4 and CASP5 are inflammatory enzymes and together with CASP1 are involved in T-cell maturation. Other names for these exemplary caspases include the following: "ICE" for CASP1; "ICH-1" for CASP2; "CPP32," "Yama," and "apopain" for CASP3; "ICE(rel)II," "TX," and "ICH-2" for CASP4; "ICE(rel)III," and "TY" for CASP5; "Mch2" for CASP6; "Mch3," "ICE-LAP3," and "CMH-1" for CASP7; "FLICE," "MACH," and "Mch5" for CASP8; "ICE-LAP6," and "Mch6" for CASP9; and "Mch4," and "FLICE-2" for CASP10.

As suggested, the current disclosure describes a combination therapy of Galeterone and a proteasome inhibitor. A combination therapy refers to those situations in which two or more different active ingredients are administered in overlapping regimens so that the subject is simultaneously exposed to both agents in therapeutically effective amounts.

Combination therapies can be used to treat subjects (humans, veterinary animals (dogs, cats, reptiles, birds, etc.) livestock (horses, cattle, goats, pigs, chickens, etc.) and research animals (monkeys, rats, mice, fish, etc.).

Therapeutically effective amounts of combination therapies disclosed herein have an anti-cancer effect. Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. For solid tumors, the formation of metastasis is a very complex process and depends on detachment of malignant cells from the primary tumor, invasion of the extracellular matrix, penetration of the endothelial basement membranes to enter the body cavity and vessels, and then, after being transported by the blood or lymph, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential.

A "tumor" is a swelling or lesion formed by an abnormal growth of cells (called neoplastic cells or tumor cells). A "tumor cell" is an abnormal cell that divides by a rapid, uncontrolled cellular proliferation and continues to divide after the stimuli that initiated the new division cease. Tumors show partial or complete lack of structural organization and functional coordination with the normal tissue, and usually form a distinct mass of tissue, which may be either benign, pre-malignant or malignant.

As used herein, an anti-cancer effect refers to a biological effect, which can be manifested by a decrease in tumor volume, a decrease in the number of cancer cells, a decrease in the number of metastases, an increase in life expectancy, or a decrease of various physiological symptoms associated with the cancerous condition. An anti-cancer effect can also be manifested by a decrease in recurrence or an increase in the time before recurrence. In particular embodiments, an anti-cancer effect also includes a statistically-significant up-regulation in AR cleavage products (e.g., 53 kDa and 41 kDa AR-V7 fragments) in a subject following administration of an active ingredient.

For administration, therapeutically effective amounts (also referred to herein as doses) can be initially estimated based on results from in vitro assays and/or animal model studies. Such information can be used to more accurately determine useful doses in subjects of interest. Particularly useful pre-clinical tests include measure of calpain activation, caspase activation, cell growth, and/or cell viability.

Calpain activation can be assessed by increased calpain activity using its substrates Ac-LLY-AFC and N-succinyl-LY-AMC (abcam; 28) in a cell-free activity assay and by the production of specific calpain substrate cleavage fragments, e.g., calpain small subunit/p28 (17), Calpastatin/p70 (18), 65-kDa fragment of PARP (19), and fragments of the microtubule-associated protein Tau in Western blotting (29).

Caspase activation can be measured by increased activities using specific substrates to caspase-9, -8 and 3 (cell-free activity assays), increased levels of the active caspases/decreased levels of pro-caspases (Western blotting and immunostaining), and the production of specific caspase substrate cleavage fragments, e.g., PARP/p89 (12-13, 21-27), and 120-kDa fragments of α-spectrin (Western blotting) (16).

Cell growth can be determined by MTT and colony formation assays. Cell counting as a golden standard can be performed routinely to determine cell doubling times and growth rates (12-13, 21-27). Cell viability can be determined by trypan blue exclusion and LDH release assays (30).

Spectrin α2 and PARP are caspase cleavage substrates. Spectrin α2 (all-spectrin) is a 285 kDa scaffolding protein expressed in most eukaryotic cells. The Spectrin heterodimer comprising all-Spectrin and any of five β-Spectrins have been found to play various roles in cellular processes including formation and maintenance of specialized plasma membrane domains, structural support of the plasma membrane and the maintenance of cell shape, and as a tumor-suppressor protein involved in TGF-β-SMAD regulation, a scaffold upon which calcium-mediated and tyrosine-phosphatase signal transduction pathways converge. An exemplary human Spectrin α2 amino acid sequence can be found at UniProtKB-Q13813 and this sequence is provided in FIG. 8.

Poly (ADP-ribose) polymerase (PARP) is a family of proteins involved in a number of cellular processes involving mainly DNA repair and programmed cell death. PARP is found in the cell's nucleus. PARPs detect and signal single-strand DNA breaks (SSB) to the enzymatic machinery involved in the SSB repair. PARP activation is an immediate cellular response to metabolic, chemical, or radiation-induced DNA SSB damage.

PARP is composed of four domains of interest: a DNA-binding domain, a caspase-cleaved domain (see below), an auto-modification domain, and a catalytic domain. The DNA-binding domain is composed of two zinc finger motifs. PARP binds sites with single-strand breaks through its N-terminal zinc fingers and recruits other proteins such as XRCC1, DNA ligase III, DNA polymerase beta, and a kinase to the site to repair the break.

Examples of proteins of the PARP family include: PARP1, PARP2, VPARP (PARP4), Tankyrase-1 and -2 (PARP-5a or TNKS, and PARP-5b or TNKS2, respectively) which are confirmed to have PARP activity; and PARP3, PARP6, TIPARP (or "PARP7"), PARP8, PARP9, PARP10, PARP11, PARP12, PARP14, PARP15, and PARP16. An exemplary human PARP1 amino acid sequence can be found at Accession: NP_001609.2, and this sequence is provided in FIG. 9.

The actual dose amount administered to a particular subject can be determined by a physician, veterinarian, or researcher taking into account parameters such as physical, physiological and psychological factors including target, body weight, stage of prostate cancer, type of prostate cancer, previous or concurrent therapeutic interventions, idiopathy of the subject, and route of administration.

Exemplary doses can include 0.05 mg/kg to 5.0 mg/kg of Galeterone and/or a proteasome inhibitor. For certain indications, the total daily dose can be 0.05 mg/kg to 30.0 mg/kg Galeterone and/or a proteasome inhibitor administered to a subject one to three times a day, including administration of total daily doses of about 0.05-3.0, 0.1-3.0, 0.5-3.0, 1.0-3.0, 1.5-3.0, 2.0-3.0, 2.5-3.0, and 0.5-3.0 mg/kg/day of administration forms of Galeterone and/or a proteasome inhibitor using 60-minute oral, intravenous or other dosing. In one particular example, doses can be administered QD or BID to a subject with, e.g., total daily doses of 1.5 mg/kg, 3.0 mg/kg, or 4.0 mg/kg of a composition with up to 92-98% wt/v of Galeterone and/or a proteasome inhibitor.

Additional useful doses can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

Doses referred to herein can include Galeterone and a proteasome inhibitor collectively or individually.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

Galeterone and a proteasome inhibitor can be administered simultaneously or within a selected time window, such as within 10 minutes, 1 hour, 3 hour, 10 hour, 15 hour, 24 hour, or 48 hour time windows or when the complementary active ingredient is within a clinically-relevant therapeutic window.

In particular embodiments, Galeterone and a proteasome inhibitor can be used in conjunction with other cancer treatments. For example, Galeterone and a proteasome inhibitor can be administered in combination with, for example, a gonadotropin-releasing hormone agonist or antagonist (e.g., Lupron, Zoladex (Goserelin), Degarelix, Ozarelix, ABT-620 (Elagolix), TAK-385 (Relugolix), EP-100 or KLH-2109); a phosphoinositide 3-kinase (PI3K) inhibitor, a TORC inhibitor, or a dual PI3K/TORC inhibitor (e.g., BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, LY-317615 (enzastaurin hydrochloride), CU-906, or CUDC-907); a CYP17 inhibitor in addition to Galeterone (e.g., abiraterone acetate (Zytiga), TAK-700 (orteronel), or VT-464); prednisone; an osteoprotective agent; a radiation therapy; a kinase inhibitor (e.g. MET, VEGFR, EGFR, MEK, SRC, AKT, RAF, FGFR, CDK4/6); Provenge, Prostvac, Ipilimumab, a PD-1 inhibitor; a taxane or tubulin inhibitor; an anti-STEAP-1 antibody; a heat shock protein 90 (HSP90) or heat shock protein 27 (HSP27) pathway modulator; an anti-androgen (e.g. bicalutamide); and/or immunotherapy.

As suggested, the active ingredients of combination therapies disclosed herein can be formulated into compositions. Each active ingredient can be formulated into its own composition for administration or active ingredients can be formulated into the same composition.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Examples of suitable aqueous and non-aqueous carriers, which may be employed in the injectable formulations include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of selected particle size in the case of dispersions, and by the use of surfactants.

Injectable formulations may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like in the compositions.

Alternatively, the composition can be in lyophilized form and/or provided in powder form for constitution with a suitable vehicle, e.g., sterile pyrogen-free water, before use. Lyophilized compositions can include less than 5% water content; less than 4.0% water content; or less than 3.5% water content.

In particular embodiments, the composition can be in a unit dosage form, such as in a suitable diluent in sterile, hermetically sealed ampoules or sterile syringes.

In particular embodiments, in order to prolong the effect of a composition, it is desirable to slow the absorption of the active ingredient(s) following injection. Compositions can be formulated as sustained-release systems utilizing semipermeable matrices of solid polymers containing at least one administration form. Various sustained-release materials have been established and are well known by those of ordinary skill in the art. Sustained-release systems may, depending on their chemical nature, release active ingredients following administration for a few weeks up to over 100 days.

In particular embodiments, delayed absorption can be accomplished by dissolving or suspending the active ingredient(s) in an oil vehicle. In particular embodiments, administration forms can be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. In addition, prolonged absorption of the injectable composition may be brought about by the inclusion of agents which delay absorption such as aluminum monostearate and gelatin.

Injectable depot forms can be made by forming microencapsule matrices of administration forms in biodegradable polymers such as polylactide-polyglycolide. Depending on the ratio of administration form to polymer, and the nature of the particular polymer employed, the rate of administration form release can be controlled. Examples of other biodegradable polymers include poly(orthoesters) and poly (anhydrides). Injectable depot formulations are also prepared by entrapping the active ingredient(s) in liposomes or microemulsions which are compatible with body tissue.

Alternatively, delayed absorption of a composition can be accomplished by the use of a liquid suspension of crystalline or amorphous material having poor water solubility. The rate of absorption of the active ingredient(s) then depends upon its rate of dissolution which, in turn, may depend upon crystal size and crystalline form.

Compositions can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

Compositions can also be formulated for oral administration. For ingestion, compositions can take the form of tablets, pills, lozenges, sprays, liquids, and capsules formulated in conventional manners. Ingestible compositions can be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable supplements with improved mouthfeel. U.S. Pat. No. 5,965,162, relates to compositions and methods for preparing comestible units which disintegrate quickly in the mouth.

Ingestible compositions may have a shape containing no sharp edges and a smooth, uniform and substantially bubble free outer coating. Coatings of ingestible compositions can be derived from a polymeric film. Such film coatings reduce the adhesion of the compositions to the inner surface of the mouth and can aid in masking potential unpleasant tastes. Coatings can also protect the compositions from atmospheric degradation. Exemplary polymeric films include vinyl polymers, cellulosics, acrylates and methacrylates, natural gums and resins such as zein, gelatin, shellac and acacia. Other common excipients used in ingestible compositions include sucrose, fructose, lactose, glucose, lycasin, xylitol, lactitol, erythritol, mannitol, isomaltose, dextrose, polydextrose, dextrin, compressible cellulose, compressible honey, compressible molasses, fondant or gums, vegetable oils, animal oils, alkyl polysiloxanes, corn starch, potato starch, pre-gelatinized starches, stearic acid, calcium stearate, magnesium stearate, zinc stearate, benzoic acid, and colorants For administration by inhalation (e.g., nasal or pulmonary), the compositions can be formulated as aerosol sprays for pressurized packs or a nebulizer, with the use of suitable propellants, e.g. dichlorodifluoromethane, trichlorofluoromethane, or dichlorotetra-fluoroethane.

As suggested, nanoparticle formulations for a variety of administration routes can also be used.

Any composition disclosed herein can advantageously include any other pharmaceutically acceptable carriers which include those that do not produce significantly adverse, allergic, or other untoward reactions that outweigh the benefit of administration, whether for research, prophylactic, and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants. Fillers and excipients are commercially available from companies such as Aldrich Chemical Co., FMC Corp, Bayer, BASF, Alexi Fres, Witco, Mallinckrodt, Rhodia, ISP, and others.

In particular embodiments, the compositions can include, for example, 25 µg/mL or mg-5 mg/mL or mg, 50 µg/mL or mg-5 mg/mL or mg, 100 µg/mL or mg-5 mg/mL or mg, 150 µg/mL or mg-5 mg/mL or mg, 200 µg/mL or mg-5 mg/mL or mg, 250 µg/mL or mg-5 mg/mL or mg, 300 µg/mL or mg-5 mg/mL or mg, 350 µg/mL or mg-5 mg/mL or mg, 400 µg/mL or mg-5 mg/mL or mg, 450 µg/mL or mg-5 mg/mL or mg, 500 µg/mL or mg-5 mg/mL or mg, 550 µg/mL or mg-5 mg/mL or mg, 600 µg/mL or mg-5 mg/mL or mg, 650 µg/mL or mg-5 mg/mL or mg, 700 µg/mL or mg-5 mg/mL or mg, 750 µg/mL or mg-5 mg/mL or mg, 800 µg/mL or mg-5 mg/mL or mg, 850 µg/mL or mg-5 mg/mL or mg, 900 µg/mL or mg-5 mg/mL or mg, 950 µg/mL or mg-5 mg/mL or mg, 1 mg/mL or mg-5 mg/mL or mg, 1.5 mg/mL or mg-5 mg/mL or mg, 2 mg/mL or mg-5 mg/mL or mg, 2.5 mg/mL or mg-5 mg/mL or mg, 3 mg/mL or mg-5 mg/mL or mg, 3.5 mg/mL or mg-5 mg/mL or mg, 4 mg/mL or mg-5 mg/mL or mg, 4.5 mg/mL or mg-5 mg/mL or mg, 25 µg/mL or mg-2.5 mg/mL or mg, 50 µg/mL or mg-2.5 mg/mL or mg, 100 µg/mL or mg-2.5 mg/mL or mg, 150 µg/mL or mg-2.5 mg/mL or mg, 200 µg/mL or mg-2.5 mg/mL or mg, 250 µg/mL or mg-2.5 mg/mL or mg, 300 µg/mL or mg-2.5 mg/mL or mg, 350 µg/mL or mg-2.5 mg/mL or mg, 400 µg/mL or mg-2.5 mg/mL or mg, 450 µg/mL or mg-2.5 mg/mL or mg, 500 µg/mL or mg-2.5 mg/mL or mg, 550 µg/mL or mg-2.5 mg/mL or mg, 600 µg/mL or mg-2.5 mg/mL or mg, 650 µg/mL or mg-2.5 mg/mL or mg, 700 µg/mL or mg-2.5 mg/mL or mg, 750 µg/mL or mg-2.5 mg/mL or mg, 800 µg/mL or mg-2.5 mg/mL or mg, 850 µg/mL or mg-2.5 mg/mL or mg, 900 µg/mL or mg-2.5 mg/mL or mg, 950 µg/mL or mg-2.5 mg/mL or mg, 1 mg/mL or mg-2.5 mg/mL or mg, 1.5 mg/mL or mg-2.5 mg/mL or mg, 2 mg/mL or mg-2.5 mg/mL or mg, 25 µg/mL or mg-1 mg/mL or mg, 50 µg/mL or mg-1 mg/mL or mg, 100 µg/mL or mg-1 mg/mL or mg, 150 µg/mL or mg-1 mg/mL or mg, 200 µg/mL or mg-1 mg/mL or mg, 250 µg/mL or mg-1 mg/mL or mg, 300 µg/mL or mg-1 mg/mL or mg, 350 µg/mL or mg-1 mg/mL or mg, 400 µg/mL or mg-1 mg/mL or mg, 450 µg/mL or mg-1 mg/mL or mg, 500 µg/mL or mg-1 mg/mL or mg, 550 µg/mL or mg-1 mg/mL or mg, 600 µg/mL or mg-1 mg/mL or mg, 650 µg/mL or mg-1 mg/mL or mg, 700 µg/mL or mg-1 mg/mL or mg, 750 µg/mL or mg-1 mg/mL or mg, 800 µg/mL or mg-1 mg/mL or mg, 850 µg/mL or mg-1 mg/mL or mg, 900 µg/mL or mg-1 mg/mL or mg, 950 µg/mL or mg-1 mg/mL or mg, 25 µg/mL or mg-750 µg/mL or mg, 50 µg/mL or mg-750 µg/mL or mg, 100 µg/mL or mg-750 µg/mL or mg, 150 µg/mL or mg-750 µg/mL or mg, 200 µg/mL or mg-750 µg/mL or mg, 250 µg/mL or mg-750 µg/mL or mg, 300 µg/mL or mg-750 µg/mL or mg, 350 µg/mL or mg-750 µg/mL or mg, 400 µg/mL or mg-750 µg/mL or mg, 450 µg/mL or mg-750 µg/mL or mg, 500 µg/mL or mg-750 µg/mL or mg, 550 µg/mL or mg-750

µg/mL or mg, 600 µg/mL or mg-750 µg/mL or mg L, 650 µg/mL or mg-750 µg/mL or mg, 700 µg/mL or mg-750 µg/mL or mg, 25 µg/mL or mg-500 µg/mL or mg, 50 µg/mL or mg-500 µg/mL or mg, 100 µg/mL or mg-500 µg/mL or mg, 150 µg/mL or mg-500 µg/mL or mg, 200 µg/mL or mg-500 µg/mL or mg, 250 µg/mL or mg-500 µg/mL or mg, 300 µg/mL or mg-500 µg/mL or mg, 350 µg/mL or mg-500 µg/mL or mg, 400 µg/mL or mg-500 µg/mL or mg, 450 µg/mL or mg-500 µg/mL or mg, 25 µg/mL or mg-250 µg/mL or mg, 50 µg/mL or mg-250 µg/mL or mg, 100 µg/mL or mg-250 µg/mL or mg, 150 µg/mL or mg-250 µg/mL or mg, 200 µg/mL or mg-250 µg/mL or mg, 25 µg/mL or mg-100 µg/mL or mg, or 50 µg/mL or mg-100 µg/mL or mg of one or more of the active ingredients.

In particular embodiments, ratios of active ingredients can include: (Galeterone:proteasome inhibitor (and whether in the same or different compositions)): 1:0.0001; 1:0.001; 1:0.005; 1:0.0075; 1:0.01; 1:0.05; 1:0.075; 1:0.1; 1:0.5; 1:0.75; 1:1; 1:1.25; 1:1.5; 1:1.75; 1:8; 1:1.2; 1:1.25; 1:1.3; 1:1.35; 1:1.4; 1:1.5; 1:1.75; 1:2; 1:3; 1:4; 1:5; 1:6:1:7; 1:8; 1:9; 1:10; 1:15; 1:20; 1:30; 1:40; 1:50; 1:60; 1:70; 1:80; 1:90; 1:100; 1:200; 1:300; 1:400; 1:500; 1:600; 1:700; 1:800; 1:900; 1:1000.

The current disclosure also provides diagnostics for CRPC treatment efficacy including systems and methods to monitor the anti-cancer effects of a CRPC therapeutic. As described herein, therapeutically effective doses of active ingredients, such as Galeterone and/or Galeterone in combination with a proteasome inhibitor results in the anti-cancer effect of cleavage of androgen receptors (ARs), including the AR-V7 variant. Detection of AR cleavage products, therefore, is indicative of an anti-cancer effect following active ingredient(s) administration. In particular embodiments, the diagnostics disclosed herein detect (e.g., measure and/or determine) levels of AR-V7 fragments, including 53 kDa and 41 kDa AR-V7 fragments. An up-regulation of AR fragments demonstrates (e.g., is indicative of) an anti-cancer effect.

In particular embodiments, the diagnostics disclosed herein detect PARP fragments and/or Spectrin α2 fragments in addition to or instead of AR fragments. The PARP fragments can be 65 kDa (p65) and 89 kDa (p89), and the Spectrin α2 fragments can be 120 kDa (p120) and 150 kDa (p150i or p150). Without being bound by theory, Galeterone treatment activates caspase-3 which produces PARP fragments of 89 kDa (PARP/p89) and Spectrin α2 fragments of 120 kDa (Spectrin α2/p120). Galeterone treatment activates caspase-3 and calpain which produces Spectrin α2 fragments of 150 kDa (Spectrin α2/p150i or p150). Galeterone treatment also activates calpain which produces PARP fragments of 65 kDa (p65). Thus, an up-regulation of these fragments is indicative of and can be used to monitor treatment efficacy.

The diagnostics disclosed herein include detecting AR fragments, PARP fragments, and/or spectrin α2 from subject samples. The detection can be qualitative or quantitative. Detected AR cleavage products can be compared to a reference level.

Methods of detecting AR, PARP and Spectrin α2 cleavage products (e.g. fragments) are well known in the art. In particular embodiments, the fragments levels can be detected using techniques for measuring and determining the serum levels of proteins. Such methods are well-known in the art and include, e.g., immunoassays based on antibodies to proteins encoded by the genes, aptamers, or molecular imprints (e.g., Western blots and ELISA). Alternatively, a suitable method can be selected to determine the activity of proteins. Such assays include protease assays, kinase assays, phosphatase assays, and reductase assays, among many others.

In embodiments, the detection of the cleavage products of AR, PARP, and/or Spectrin α2 in circulating tumor cells (in blood) can be used as to predict resistance to enzalutamide, abiraterone, and other AR-targeted agents. A Western blot assay can be used to detect the blood levels of AR or AR-V7 cleavage fragments, PARP, and/or Spectrin α2 that could then be used in selection criteria to monitor and select patients in a clinical trial as well as to monitor the activity of Gal and proteasome inhibitor.

In particular embodiments, a "reference level" can refer to a standardized value for AR, AR-V (e.g., AR-V7), PARP, and/or Spectrin α2 cleavage product biomarkers which represents a level not associated with any disease; a level associated with a particular stage of the disease (i.e., hormone dependent or hormone refractory (CRPC)); or a level associated with a particular subject at the time of diagnosis, at the beginning of treatment, or at a time point during a treatment, such as at a time point following Galeterone and proteasome inhibitor administration. The reference level can be a universal reference level which is useful across a variety of testing locations or can be a reference level specific for the testing location and specific assay used to measure the cleavage product biomarkers. In particular embodiments, the reference level is derived from (i) an individual who does not have prostate cancer; (ii) a group of individuals who do not have prostate cancer; (iii) a subject before diagnosis of prostate cancer; or (iv) a subject at the time of diagnosis, at the beginning of a treatment regimen for prostate cancer or at particular time points during a treatment. Reference levels for a subject can also be related to time points of a subject not undergoing treatments to monitor the natural progression or regression of the disease.

In particular embodiments, the levels of AR, AR-V (e.g., AR-V7), PARP, and/or Spectrin α2 cleavage product biomarkers, can be determined sequentially over time. In particular embodiments, the cleavage product biomarker levels can be determined 1 time, 2 times, 3 times, 4 times, 5 times, 6 times, 7 times, 8 times, 9 times, 10 times and every remaining integer up to 100 times or more. In a subject at risk of having CRPC, the cleavage product biomarkers, levels can be determined weekly, monthly, every 2 months, every 3 months, every 4 months, every 5 months, every 6 months, every 7 months, every 8 months, every 9 months, every 10 months, or every 11 months, or yearly to determine if the subject has prostate cancer or to determine if a treatment has been effective or ineffective, or a prostate cancer is progressing or regressing (i.e., each measure can provide an intra-subject reference level).

In a subject undergoing treatment for prostate cancer, the AR, AR-V (e.g., AR-V7), PARP, and/or Spectrin α2 cleavage product biomarker levels can be determined weekly, monthly, every 2 months, every 3 months, every 4 months, every 5 months, every 6 months, every 7 months, every 8 months, every 9 months, every 10 months, or every 11 months, or yearly to determine if the prostate cancer in the subject has progressed, has regressed, or has been successfully or unsuccessfully treated. In particular embodiments, a single determination of AR and/or AR-V7 cleavage product, PARP, and/or Spectrin α2 biomarkers is used in the disclosed methods.

Diagnostics disclosed herein may be particularly useful to predict when a subject may become refractory to hormone treatments.

In particular embodiments, the biomarkers are measured and determined from a biological sample such as blood, plasma, or serum. The blood sample could contain peripheral blood.

Reductions in the described measures can also indicate spontaneous remission of the disease and/or the effectiveness of a treatment regimen.

As used herein, "unchanged" measures are evaluated in relation to a previous comparison in the same subject and denote a failure to achieve a statistically significant change in a score towards or away from a reference level in the particular subject.

The present disclosure further provides for kits including one or more treatment options (e.g., combination therapies) and/or diagnostic assays for practicing any of the methods disclosed herein. The kits may include a notice in the form prescribed by a governmental agency regulating the manufacture, use or sale of pharmaceuticals, biological products, lab developed tests, etc., which notice reflects approval by the agency of the manufacture, use or sale for human administration and/or testing. Treatment portions of the kits may include active ingredient(s) in a ready-to-use form and/or a form that requires preparation before administration (e.g., lyophilized). Diagnostic portions of the kits may utilize any necessary or appropriate polypeptides, conjugates, antibodies, polynucleotides, expression vectors, cells, methods, compositions, systems, and/or apparatuses useful for the detection of AR or AR-V fragments such as the 53 kDa and/or the 41 kDa fragment of AR-V7, PARP, and/or Spectrin α2. The kits may also include syringes, pipettes, antiseptics, tubing, gloves, diluents, etc. as well as instructions for practicing any method described herein which may include relevant reference levels. Optionally reference levels are determined using the detection kits.

In particular embodiments of the kits, the kit includes one of more diagnostic assays for detecting intact AR-V7 and AR-V7 fragments such as the 53 kDa and/or the 41 kDa fragments. In particular embodiments of the kits, the kit includes one of more diagnostic assays for detecting PARP cleavage products including 89 kDa and 65 kDa PARP fragments, and Spectrin α2 cleavage products including 120 kDa and 150 kDa Spectrin α2 fragments.

In particular embodiments, the kit includes three or more diagnostic assays, four or more diagnostic assays, five or more diagnostic assays, six or more diagnostic assays, seven or more diagnostic assays, or eight or more diagnostic assays.

The Exemplary Embodiments and Example below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A method of providing an anti-cancer effect in a subject having cancer (e.g., castration-resistant prostate cancer (CRPC) or multiple myeloma (MM)) comprising administering therapeutically effective amounts of Galeterone and a proteasome inhibitor to the subject, thereby providing an anti-cancer effect in the subject.

2. A method of embodiment 1 wherein Galeterone has the structure

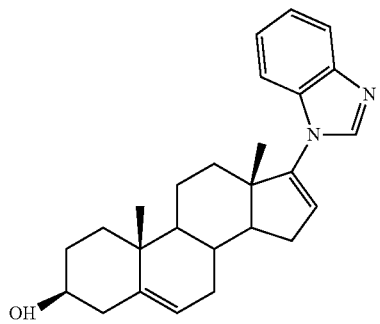 [SMILES: C[C@]12CC[C@H](O)CC1=CCC1C2CC[C@]2(C)C(n3cnc4ccccc43)=CCC12]

3. A method of embodiment 1 or 2 wherein the proteasome inhibitor is selected from β-lapachone, bortezomib, brotezamide, carfilzomib, CEP-18770, disulfiram, epigallocatechin-3-gallate, epoxomicin, lactacystin, laxomib (MLN9708), MG132, MLN9708, oprozomib (ONX 0912), salinosporamide A (NPI-0052, marizomib), or an immunoproteasome inhibitor.

4. A method of embodiment 3 wherein the proteasome inhibitor is bortezomib.

5. A method of potentiating the anti-cancer effect of Galeterone comprising administering a therapeutically effective amount of a proteasome inhibitor in combination with a therapeutically effective amount of Galeterone to a subject in need thereof.

6. A method of embodiment 5 wherein the subject in need thereof has castration-resistant prostate cancer (CRPC) or multiple myeloma (MM).

7. A method of embodiment 5 or 6 wherein Galeterone has the structure

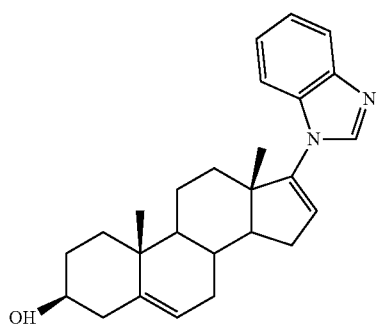 [SMILES: C[C@]12CC[C@H](O)CC1=CCC1C2CC[C@]2(C)C(n3cnc4ccccc43)=CCC12]

8. A method of any of embodiments 5-7 wherein the proteasome inhibitor is selected from β-lapachone, bortezomib, brotezamide, carfilzomib, CEP-18770, disulfiram, epigallocatechin-3-gallate, epoxomicin, lactacystin, laxomib (MLN9708), MG132, MLN9708, oprozomib (ONX 0912), salinosporamide A (NPI-0052, marizomib), or an immunoproteasome inhibitor.

9. A method of embodiment 8 wherein the proteasome inhibitor is bortezomib.

10. A composition comprising Galeterone and a proteasome inhibitor.

11. A composition of embodiment 10 wherein Galeterone has the structure

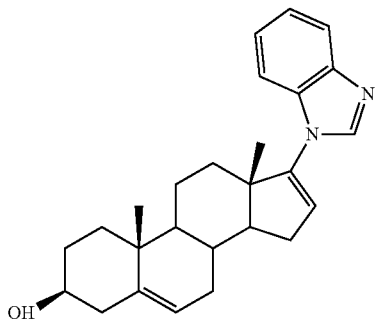 [SMILES: C[C@]12CC[C@H](O)CC1=CCC1C2CC[C@]2(C)C(n3cnc4ccccc43)=CCC12]

12. A composition of embodiment 10 or 11 wherein the proteasome inhibitor is selected from β-lapachone, bortezomib, brotezamide, carfilzomib, CEP-18770, disulfiram, epigallocatechin-3-gallate, epoxomicin, lactacystin, laxomib (MLN9708), MG132, MLN9708, oprozomib (ONX 0912), salinosporamide A (NPI-0052, marizomib), or an immunoproteasome inhibitor.

13. A composition of embodiment 12 wherein the proteasome inhibitor is bortezomib.

14. A method of monitoring an anti-cancer effect of a castration-resistant prostate cancer (CRPC) therapeutic composition following its administration to a subject comprising detecting an androgen receptor (AR, e.g. SEQ ID NOs: 1-2) cleavage product, a Poly (ADP-ribose) polymerase (PARP, e.g. SEQ ID NO: 4) cleavage product, and/or a Spectrin aII (e.g. SEQ ID NO: 3) cleavage product in a sample obtained from the subject following the administration wherein presence of the AR cleavage product, PARP cleavage product, and/or Spectrin αII cleavage product is indicative of the anti-cancer effect.

15. A method of embodiment 14 wherein the AR cleavage product is an AR variant (e.g. SEQ ID NO: 2) cleavage product.

16. A method of embodiment 15 wherein the AR variant cleavage product is an AR-variant 7 (AR-V7) cleavage product.

17. A method of embodiment 16 wherein the AR-V7 cleavage product is a 53 kDa or a 41 kDa AR-V7 fragment.

18. A method of any of embodiments 14-17 wherein the PARP cleavage product is PARP/p65 and/or PARP/p89.

19. A method of any of embodiments 14-18 wherein the Spectrin αII cleavage product is Spectrin αII/p120 and/or Spectrin αII/p150 or 150i.

20. A method of monitoring an anti-cancer effect of a castration-resistant prostate cancer (CRPC) therapeutic composition following its administration to a subject comprising detecting a PARP cleavage product (e.g. cleavage product of SEQ ID NO: 4) and/or a Spectrin α2 cleavage product (e.g. cleavage product of SEQ ID NO: 3) in a sample obtained from the subject following the administration wherein presence of the PARP cleavage product and/or Spectrin α2 cleavage product is indicative of the anti-cancer effect.

21. The method of embodiment 20, wherein the PARP cleavage product is PARP/p65 and/or PARP/p89.

22. The method of embodiment 20 or 21, wherein the Spectrin α2 cleavage product is Spectrin α2/p120 and/or Spectrin α2/p150 or p150i.

23. A kit for practicing a method of any of embodiments 1-9 or 14-22, alone or in combination.

24. A kit comprising a composition of any of embodiments 10-13, alone or in combination.

25. A method to target 19S proteasome-associated DUBs and 20s proteasome comprising administering therapeutically effective amounts of Galeterone and a proteasome inhibitor in vivo or in vitro thereby targeting 19S proteasome-associated DUBs with Galeterone and 20s proteasome with the proteasome inhibitor.

26. A method of embodiment 25 wherein Galeterone has the structure

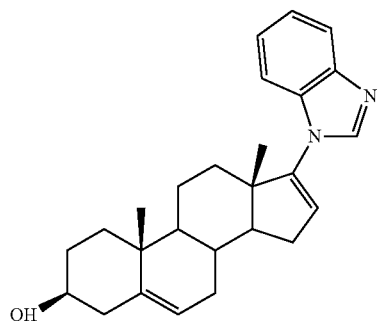 [SMILES: C[C@]12CC[C@H](O)CC1=CCC1C2CC[C@]2(C)C(n3cnc4ccccc43)=CCC12]

27. A method of embodiment 25 or 26 wherein the proteasome inhibitor is selected from β-lapachone, bortezomib, brotezamide, carfilzomib, CEP-18770, disulfiram, epigallocatechin-3-gallate, epoxomicin, lactacystin, laxomib (MLN9708), MG132, MLN9708, oprozomib (ONX 0912), salinosporamide A (NPI-0052, marizomib), or an immunoproteasome inhibitor.

28. A method of embodiment 27 wherein the proteasome inhibitor is bortezomib.

29. A method to target DUBs in solid and/or liquid tumors comprising administering a therapeutically effective amount of Galeterone to a subject in need thereof thereby targeting DUBs in solid and/or liquid tumors.

30. A method of embodiment 29 wherein the targeting provides an anti-cancer effect.

31. A method of embodiment 29 or 30 wherein Galeterone has the structure

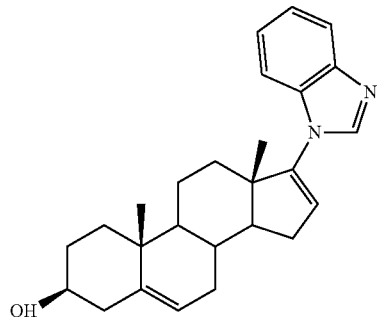 [SMILES: C[C@]12CC[C@H](O)CC1=CCC1C2CC[C@]2(C)C(n3cnc4ccccc43)=CCC12]

32. A method of any of embodiments 29-31 further comprising administering a therapeutically effective amount of a proteasome inhibitor.

33. A method of embodiment 32 wherein the proteasome inhibitor is selected from β-lapachone, bortezomib, brotezamide, carfilzomib, CEP-18770, disulfiram, epigallocatechin-3-gallate, epoxomicin, lactacystin, laxomib (MLN9708), MG132, MLN9708, oprozomib (ONX 0912), salinosporamide A (NPI-0052, marizomib), or an immunoproteasome inhibitor.

34. A method of embodiment 33 wherein the proteasome inhibitor is bortezomib.

Example 1

Background: Abiraterone (Abi) acetate and Enzalutamide (Enz) are two newly FDA-approved antiandrogen receptor (anti-AR) agents for treating castrate-resistant prostate cancer (CRPC) (1-3).

Abiraterone (Abi) is a steroidal antiandrogen, specifically an androgen synthesis inhibitor, used in combination with prednisone in metastatic CRPC. After an expedited six-month review, abiraterone acetate was approved by the US Food and Drug Administration (FDA) in April 2011. In phase III clinical trials, it extended median survival to 14.8 months versus 10.9 months placebo, and the trial was stopped early because of the successful outcome.

Abi acetate, an orally active agent, is converted in vivo to Abi, a specific and irreversible inhibitor of CYP17, resulting in significant decrease in testosterone levels (1-3). This is because CYP17 catalyzes two sequential reactions: (a) the conversion of pregnenolone and progesterone to their 17α-hydroxy derivatives by its 17α-hydroxylase activity, and (b) the subsequent formation of dehydroepiandrosterone (DHEA) and androstenedione, respectively, by its 17,20-lyase activity. DHEA and androstenedione are androgens and precursors of testosterone. Inhibition of CYP17 activity by abiraterone thus decreases circulating levels of androgens such as DHEA, testosterone, and dihydrotestosterone (DHT).

Enzalutamide (Enz) is a synthetic, non-steroidal pure antiandrogen which was developed by the pharmaceutical company Medivation for the treatment of metastatic CRPC. It was FDA-approved in August, 2012. PSA level decreased more than 50% in 40/65 chemo-naive patients and 38/75 chemotherapy-treated patients. In November 2011, this trial was stopped early after an interim analysis revealed that patients given the drug lived for approximately 5 months longer than those taking placebo.

Although both Abi and Enz have shown impressive results, resistance in CRPC patients has already been observed (1-3). One of the major resistance mechanisms is related to constitutively active forms of ARs with C-terminal loss or lacking of a functional LBD (4). AR-V7 is the most common form of C-terminal loss (4).

Galeterone (TOK-001 or VN/124-1) is a novel steroidal antiandrogen under development by Tokai Pharmaceuticals for the treatment of prostate cancer. Galeterone acts by disrupting the androgen receptor signaling pathway. This pathway is activated by the binding of male hormones (also known as androgens), such as testosterone and dihydrotestosterone (DHT) to androgen receptors in prostate cancer cells. Galeterone disrupts the activation of the androgen receptor pathway in three ways: Androgen receptor degradation, CYP17 enzyme inhibition and inhibition of androgen binding to the androgen receptor.

Galeterone has been tested in a Phase 2 clinical trial (ARMOR2) as a treatment for patients with CRPC (6-7). It has been found that Abi- and Enz refractory CRPC patients with C-terminal AR loss remain responsive to Gal (6-7). A Gal Phase 3 trial, the first precision medicine-based trial in AR-V7-positive metastatic CRPC patients started in the summer of 2015.

Gal has been shown to induce degradation of AR and AR-V7 proteins under preclinical conditions (8). Further, it was suggested that Gal-induced AR-V7 (and AR) protein depletion was through degradation by proteasomes (9), for which one of the supporting evidence is that Gal-induced AR-V7 degradation could be inhibited by 5 µM of MG132 (9). However, MG132 at 5 µM can inhibit both proteasome ($IC_{50}$=100 nM) and calpain ($IC_{50}$=1.2 µM) activities (10-11). Therefore Gal's mechanism of action requires careful investigation.

The medicinal compound Celastrol, which has a chemical structure related to that of Gal, is a potent proteasome inhibitor which suppresses human PC growth in nude mice, associated with decreased AR protein (12; the Cancer Res Cover Story). Celastrol and other proteasome inhibitors can decrease levels of AR protein in prostate cancer cells via activation of a calpain-like activity (13). In the study described below, the effect of Gal on the proteasome, calpain and AR-V7 protein in CRPC cells was examined.

Figure 1A:
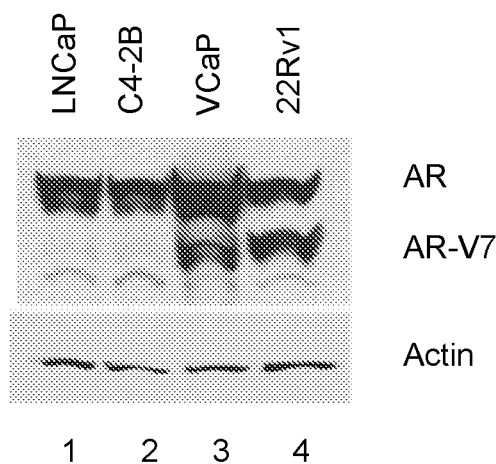
FIG. 1A. Western blotting with anti-N20/AR antibody to examine levels of AR and AR-V7 proteins in various prostate cancer cell lines.

It was first confirmed that VCaP and 22Rv1 CRPC cells express high AR-V7 protein (14-15), compared to LNCaP and C4-2B cells (FIG. 1A) and that treatment of 20 µM Gal for 66-72 h decreased AR-V7 protein expression (FIG. 1B, lanes 2 vs. 1, and 6 vs. 5) (8-9).

Gal treatment causes activation of calpains and caspases prior to the decrease in AR-V7 protein expression. Detailed kinetics of Gal-induced AR-V7 protein depletion (FIG. 2A) was investigated next. 22Rv1 cells were treated with 20 µM of Gal for up to 72 h, followed by Western blotting with specific anti-AR-V7 monoclonal antibody (Precision, AG10008, that can selectively detect AR-V7 protein) and anti-AR N20 antibody (that can recognize both full length AR, AR-V7 and other AR-V proteins). Levels of full length AR (AR-FL) protein were decreased after 48 h; however, AR-V7 protein expression remained high after up to 56 h and decreased significantly between 64-68 h, and became undetectable at 72 h (FIG. 2A, a).

Possible activation of caspases and calpains in these CRPC cells during Gal treatment was investigated. As shown in FIG. 2B, caspase-3 activity was increased after 24 h and reached to the highest after 48 h. Consistently, the production of caspase-3-specific cleavage substrates, PARP fragment of 89 kDa (PARP/p89) and Spectrin α2/p120 (16) were detected along with caspase-3 activation (FIG. 2B, c-d). Both caspase-3 and calpain can also cleave Spectrin α2 into fragments with a similar size, 150 kDa (p150i or p150) (FIG. 2A, d; 16).

Calpain activation is associated with the production of a 28 kDa cleavage fragment (p28) of calpain small subunit (17). It was found that in Gal-treated cells, a p28 fragment appeared between 48 and 72 h, as detected by a specific antibody to the 30 kDa calpain small subunit (FIG. 2A, e). Consistently, another calpain cleavage product, Calpastatin/p70 (18) was detected at the same time points (FIG. 2A, f). It has been shown that calpain cleaves PARP into a 65 kDa fragment (19); two peaks of PARP/p65, at approximately 4 and 68 hours, respectively (FIG. 2A, c) were found, which suggests early and late calpain activations. These results show that Gal induces activation of both caspase-3 and (early) calpain prior to AR-V7 depletion.

Figure 1B:
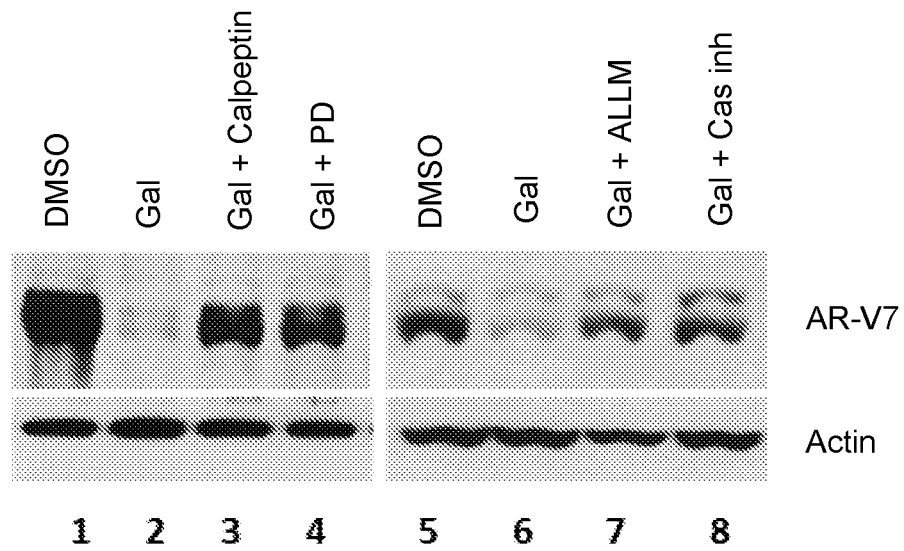
FIG. 1B. Inhibition of calpain or caspase could rescue AR-V7 degradation induced by Gal. Lanes 1-4, 22Rv1 cells were treated with 20 μM of Gal (DMSO as a control) without or with a calpain inhibitor, 40 μM of calpeptin or PD 156060 (PD) for 66 h. Lanes 5-8, 22Rv1 cells treated with 20 μM of Gal (DMSO as a control)

Gal-induced AR-V7 loss can be blocked by a specific inhibitor to calpain or caspases. Whether calpains and/or caspases are involved in Gal-induced AR-V7 degradation was further determined. As shown in FIG. 1B, addition of any one of the three specific calpain inhibitors, calpeptin (Z-Leu-Nle-CHO), PD150606 or N-acetyl-L-leucyl-L-leucyl-L-methioninal (ALLM), was able to rescue AR-V7 loss partially (FIG. 1B, lanes 1-7). Furthermore, a pan-caspase inhibitor was able to suppress Gal-induced AR-V7 decrease (FIG. 1B; lanes 8 vs. 6). These results support the contribution of calpains & caspases to AR-V7 protein depletion by Gal treatment.

The FDA-approved, specific 20S proteasome inhibitor Bortezomib is unable to block, rather increasing Gal-induced AR-V7 degradation. To confirm the involvement of proteasomes in Gal-induced AR-V7 protein degradation (8-9), Bortezomib (BTZ), the first FDA approved specific 20S proteasome inhibitor (20) was used. Reproducibly, 72 h treatment with 20 µM Gal caused loss of AR-V7 protein in 22Rv1 cells (FIG. 3A, lanes 2 vs. 1; also see FIGS. 1B, 2A). However, addition of BTZ at up to 40 nM did not rescue the loss of AR-V7 protein by Gal (FIG. 3A, lanes 3-6 vs. 2 vs. 1); as a control, BTZ alone caused a dose-dependent inhibition of proteasomal chymotrypsin (CT)-like activity (FIG. 3B, DMSO bars). In addition to the inability to inhibit Gal-mediated AR-V7 protein degradation, BTZ alone (without Gal) caused a dose-dependent decrease in AR-V7 protein expression (FIG. 3A, lanes 7-10 vs. 1), demonstrating that specific proteasome inhibition leads to AR-V7 protein depletion.

Figure 4A:
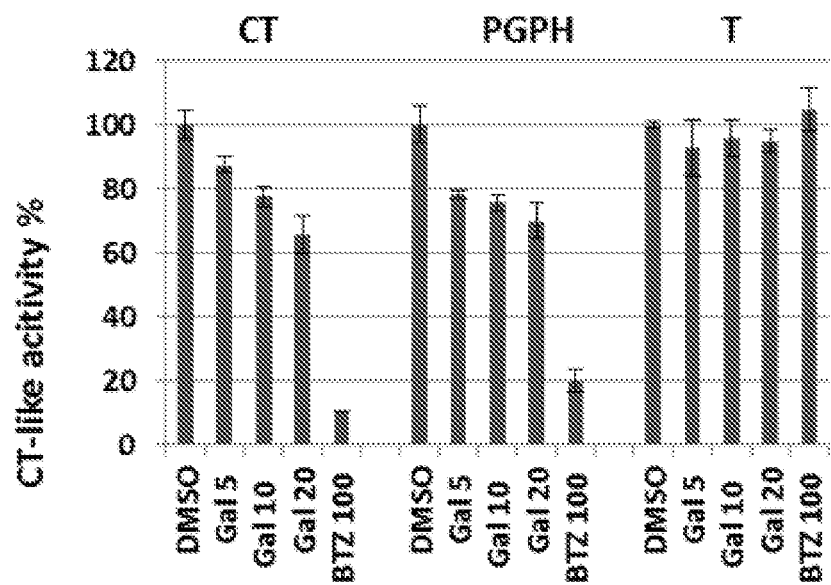
Figure 4B:
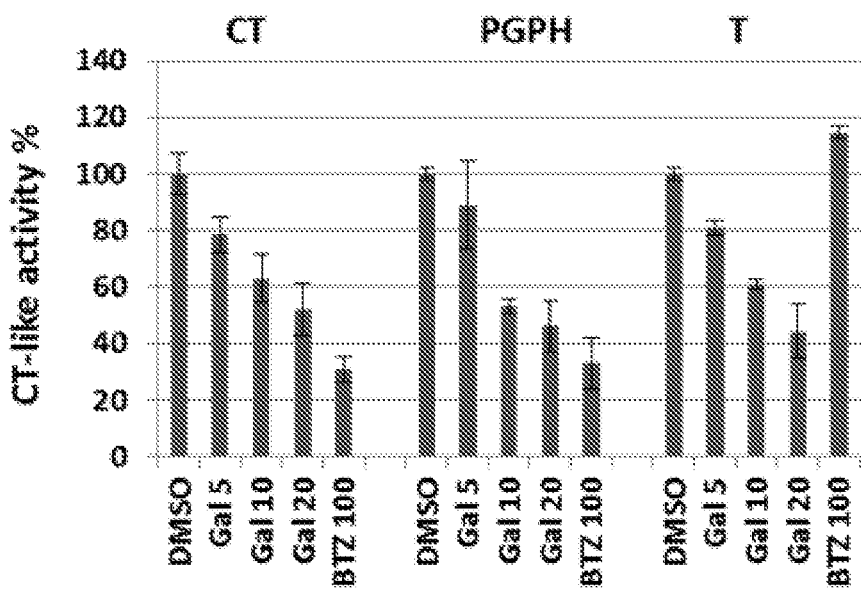
Figure 4C:
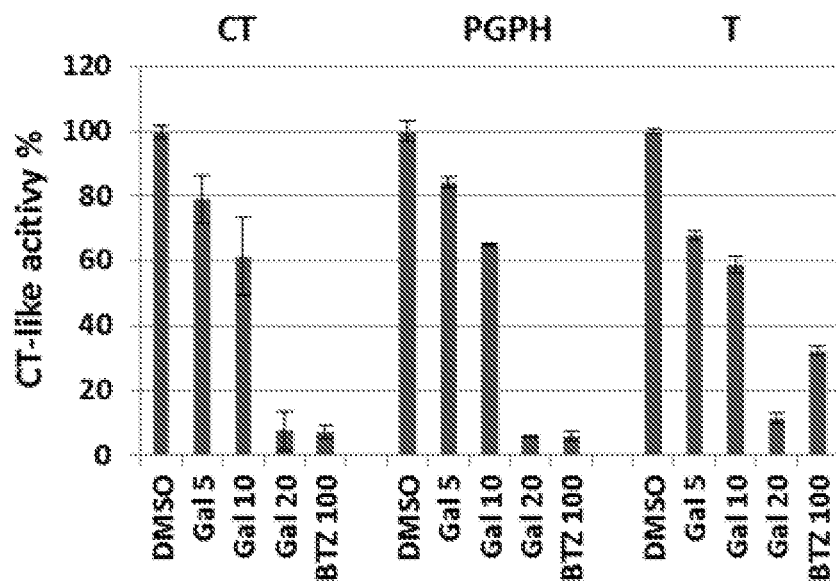
Figure 4D:
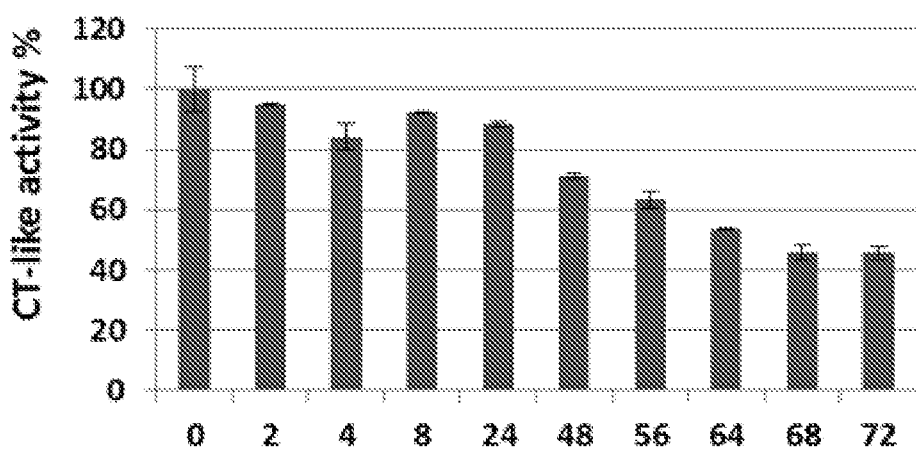

FIG. 2A shows that Gal treatment induced AR-V7 protein depletion after 64 h, but not 48 h or earlier. It was then investigated, under such a condition, whether BTZ could sensitize the CRPC cells to Gal by increasing AR-V7 protein degradation. While again Gal treatment for 48 h was not sufficient to decrease expression of AR-V7 protein (FIG. 3C, lanes 2 vs. 1), addition of BTZ, especially at 20 nM to Gal-treated cells resulted in a dose-dependent AR-V7 protein depletion (FIG. 3C, lanes 3-6 vs. 2 vs. 1). As a control, BTZ treatment for 48 h caused proteasomal CT-like inhibition (FIG. 3D, DMSO bars). Therefore, the proteasome inhibitor BTZ not only caused AR-V7 depletion but also increased Gal-induced AR-V7 degradation, suggesting the beneficial use of combination therapies of Gal and second generation proteasome inhibitors for CRPC patients. Consistently, in the same experiment, increased levels of PARP cleavage were detected in the combination treated groups, Gal treatment of CRPC cells causes a reduction in levels of all three proteasome activities. Since both Gal and BTZ decrease levels of AR-V7 protein expression (FIGS. 1-3; refs. 8-9), whether Gal treatment alone affects levels of cellular proteasome activities in CRPC cells was examined. Exposure of 22Rv1 cells to 5-20 µM Gal for 24 h resulted in a dose-dependent decrease in levels of proteasomal CT-like and peptidyl-glutamyl peptidehydrolyzing (PGPH)-like, but not trypsin (T)-like activities (FIG. 4A; 100 nM BTZ as a control); after 48 h treatment, all three proteasomal activities were decreased in a Gal dose-dependent fashion (FIG. 4B). When VCaP cells were treated with 5-20 µM Gal for 72 h, a dose-dependent inhibition of the three proteasomal activities was again observed (FIG. 4C). To study how early Gal causes proteasome inhibition, a detailed kinetic experiment in 22Rv1 cells was performed, and it was found that addition of Gal caused a time-dependent proteasome CT inhibition: 10% between 2-24 h, 30% at 48 h and >50% after 64 h (FIG. 4D). Therefore, Gal-induced proteasome inhibition occurs prior to activation of calpain/caspases and loss of AR-V7 protein (FIGS. 4 vs. 2).

Because both Gal and BTZ cause proteasome inhibition (FIG. 4; 20), it was then determined the effect of their combination on CRPC cellular proteasome activities. It was found that the combination of Gal and BTZ resulted in a further inhibition of the proteasomal CT-like activity, compared to each drug alone (FIG. 3B, D), supporting the idea that both Gal and BTZ inhibit the proteasome activity independently.

Cleavage of nuclear AR-V7 protein into fragments of 53 kDa and 41 kDa after Gal treatment: Cellular localizations of AR-V7/AR proteins, calpain/caspase substrate proteins and their cleavage fragments was also examined using cytosolic and nuclear fractions isolated from Gal-treated R22v1 cells (FIG. 5A). By using AR-V7 specific monoclonal antibody, it was observed that, prior to Gal addition, most of AR-V7 protein was in the nuclear fraction (FIG. 5A, a, b, lanes 1 vs. 6). After 8-24 h treatment with Gal, AR-V7 band decreased, associated with an appearance of at least two lower bands of 53 kDa and 41 kDa, both of which were increased at 48 h (FIG. 5A, a, b, lanes 2-4). At 72 h, the nuclear ARV7 was decreased significantly, while mainly the 53 kDa fragment was detected (FIG. 5A, a, b, lane 5). The levels of cytosolic AR-V7 protein were decreased only at 72 h (FIG. 5A, a, b, lanes 6-10). When anti-AR amino terminal (N20) antibody was used (FIG. 5A, c), a decrease in both cytosolic and nuclear AR-FL protein expression was detected after Gal treatment. Anti-N20 antibody also detected several potential AR-Vs in both fractions, all of which were decreased at 72 h (FIG. 5A, c). The caspase 3-specific product PARP/p89 was found in nuclear fraction (FIG. 5A, d), while the calpain cleavage product Calpastatin/p70 was found mainly in the cytosolic fraction (FIG. 5A, g). Spectrin α2 fragments of 150 kDa (caspase-3 or calpain cleavage fragment) and 120 kDa (caspase-3 cleavage product) as well as calpain small/p28 (calpain cleavage product) were detected in both cytosolic and nuclear fractions (between 24-72 h) (FIG. 5A, e-f). (FIG. 5B-D).

Figure 5B:
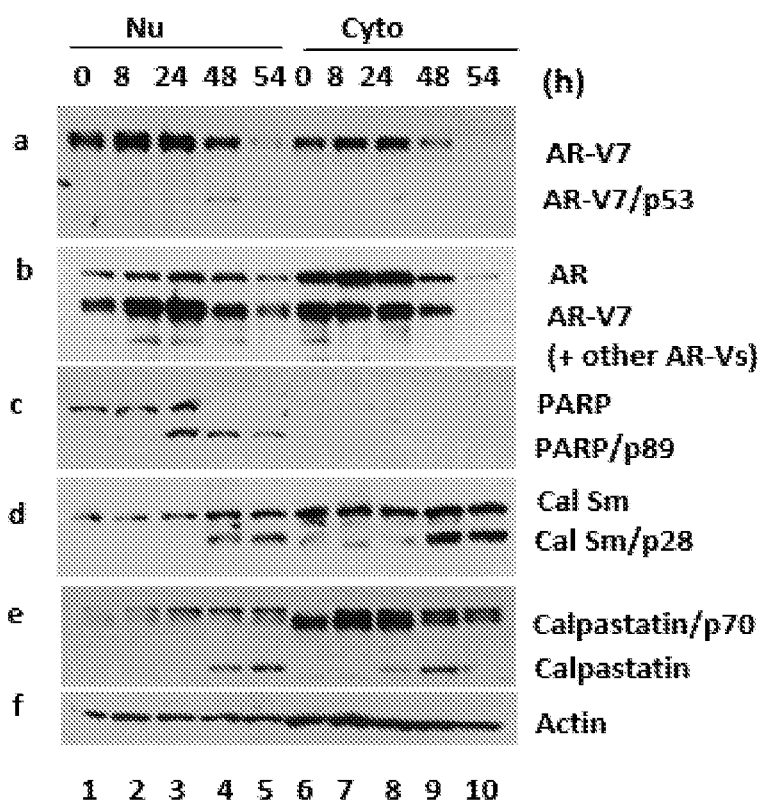
Figure 5C:
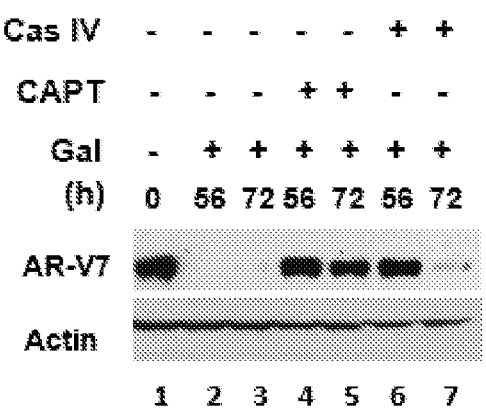
Figure 5D:
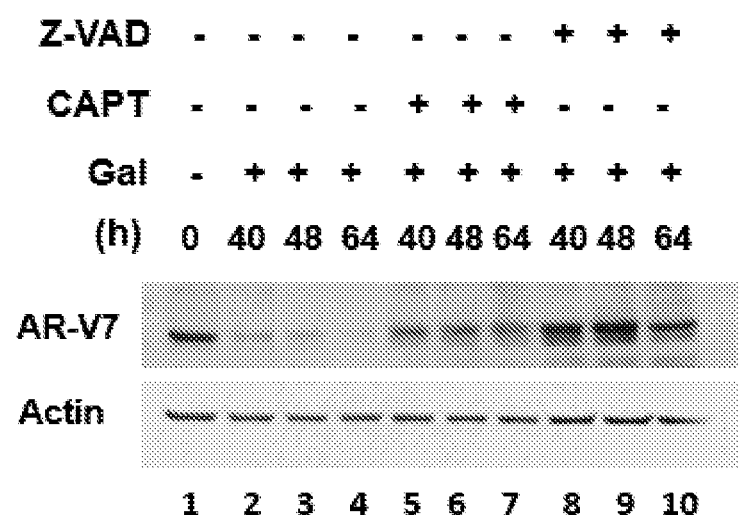

22Rv1 cells were first androgen-starved for 24 h, followed by Gal treatment for up to 56 h and preparation of cellular fractions (FIG. 5B). Consistent with previous report (20), androgen starvation did not change AR-V7 primary nuclear localization (FIG. 5B, a). Nuclear AR-V7 was again decreased in the time-dependent manner. A cleaved band of ~53 kDa was again detected in the nuclear fraction after 24-48 h treatment (FIG. 5B, a). A similar fragment was also detected by using the anti-AR (N20) antibody between 8 and 48 h (FIG. 5B, b). Along with nuclear AR-V7 decrease was activation of nuclear calpain, evidenced by increased levels of its specific cleavage substrates, Cal Sm/p28 and Calpastatin/p70 (FIG. 5B, d-e). These calpain cleavage fragments were also found in the cytosolic fraction (FIG. 2A, d-e). The caspase-3-specific cleavage fragment PARP/p89 was found only in the nuclear fraction (FIG. 5B, c). These results indicate that calpain and caspase activation are correlated with cleavage of AR-V7 protein in CRPC nuclei.

Inhibitors of calpain and caspases block the nuclear AR-V7 degradation in Gal-treated CRPC cells. Then we tested whether an inhibitor of calpain or caspase could rescue AR-V7 degradation induced by Gal treatment. 22Rv1 cells were treated with Gal in the absence or presence of the specific calpain inhibitor calpeptin or a pan-caspase inhibitor, followed by isolation of cytosolic and nuclear fractions. As shown in FIG. 5C, Gal induced the nuclear AR-V7 depletion after 56 h or 72 h, which could be blocked by addition of calpeptin, a calpain inhibitor at both time points (lanes 4-5 vs. 1-3; a pan-caspase inhibitor IV was able to rescue Gal-induced nuclear AR-V7 loss significantly at 56 h, but only slightly at 72 h (FIG. 5C, lanes 6-7). Similarly, when androgen-starved 22Rv1 cells were used for another inhibitor experiment, Gal treatment decreased levels of nuclear AR-V7 protein after 40, 48 and 64 h (FIG. 5D, lanes 1-4). Addition of Calpeptin partially rescued AR-V7 loss by Gal (FIG. 5D, lanes 5-7), while another pan-caspase inhibitor Z-VAD was able to block the Gal-induced AR-V7 depletion (FIG. 5D, lanes 8-10). The inhibitor experiments further support the involvement of calpain and caspases in the depletion of AR-V7 protein during Gal treatment.

The described results show that Gal treatment of CRPC cells: (i) decreased cellular proteasome activity (FIGS. 3-4); (ii) activated calpains and caspases (FIGS. 1-2); (iii) caused AR-V7 degradation (FIGS. 1-3; consistent with Refs. 8-9); (iv) Gal-induced AR-V7 depletion is likely due to degradation by calpains and caspases but not 20S proteasome; (v) BTZ sensitizes CRPC cells to Gal-induced AR-V7 degradation, associated with increased proteasome inhibition; (vi) For the first time, specific AR-V7 fragments of 53 kDa and 41 kDa were detected, associated with AR-V7 decrease in the nuclei of R22v1 cells after Gal treatment (FIG. 5); (vii) Nuclear AR-V7 cleavage was accompanied by activation of caspase-3 and calpain (FIG. 5).

Example 2

Galeterone inhibits activities of 19S proteasome-associated Deubiquitinating enzymes (DUBs) in castrate resistant prostate cancer (CRPC) cells and sensitizes bortezomib-resistant multiple myeloma (MM) cells.

Figure 10A:
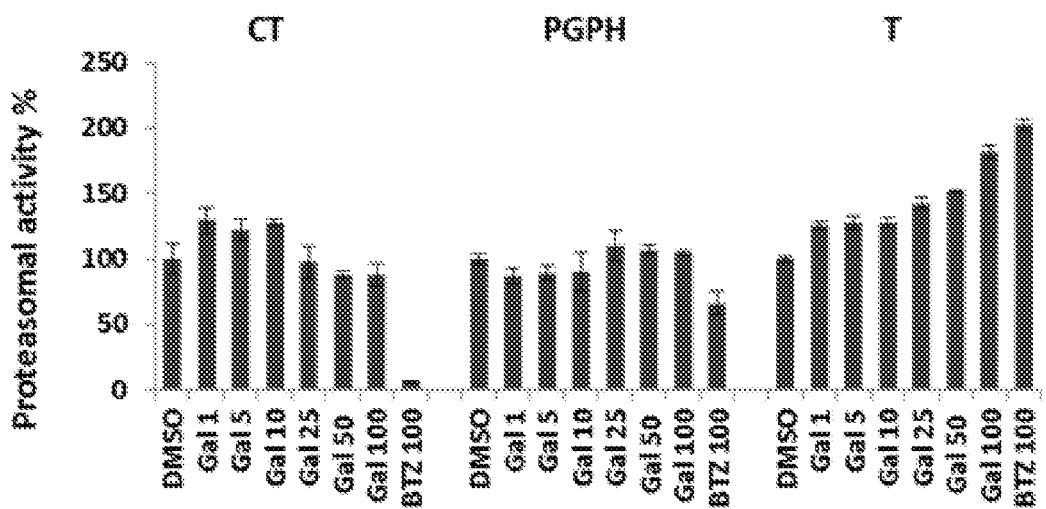
Figure 10B:
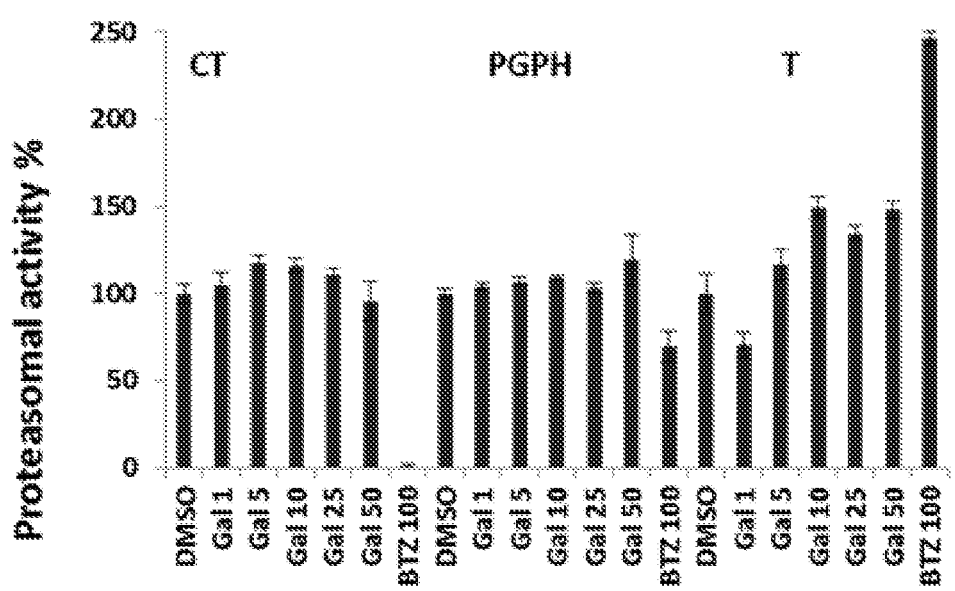
Figure 10C:
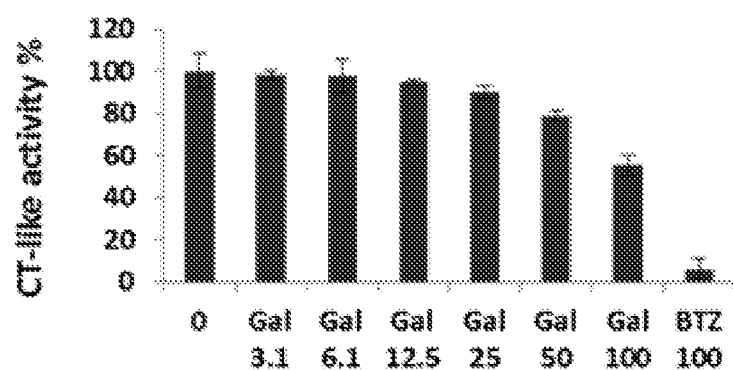
Figure 10D:
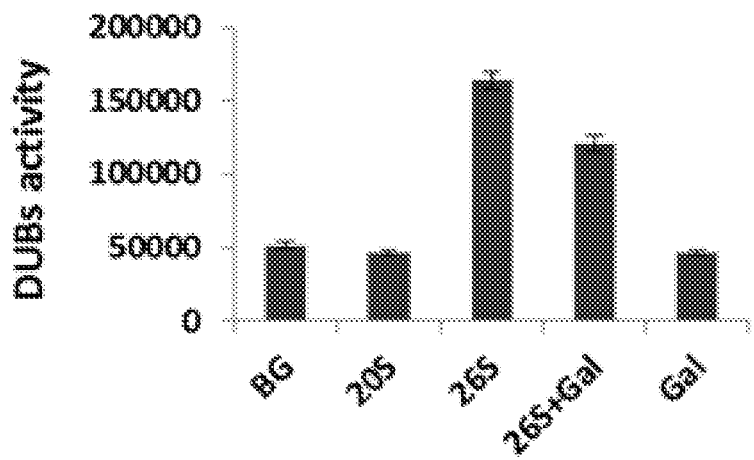
Figure 10E:
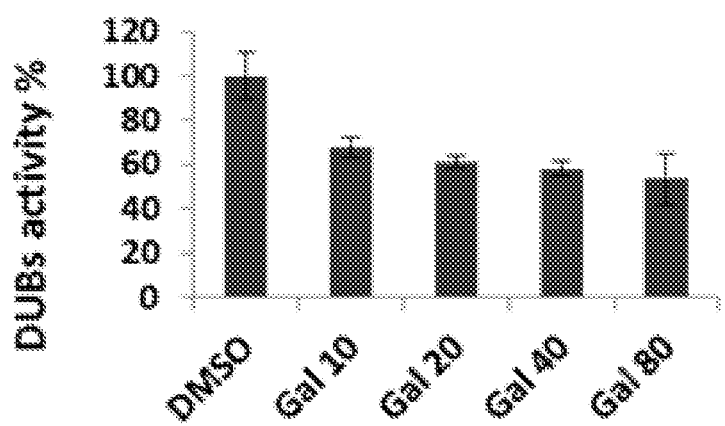

Previously it was found that Gal inhibits the chymotrypsin-like (CT-like) activity of the proteasome in prostate cancer cells. Whether Gal is a direct inhibitor of the proteasome was of interest. All of the three proteasomal activities of purified 20S or 26S proteasomes in the presence of Gal were determined. As shown in FIGS. 10A and 10B, Gal was unable to block all the three proteasomal activities (CT, PGPH and T-like activities) when purified 20S or 26S proteasomes were used. When a protein extract of 22Rv1 cells was used, Gal could inhibit the CT-like activity of the proteasome at high concentrations (50 or 100 μM) (FIG. 10C). These results suggest that Gal might target the 19S proteasome rather than the 20S proteasome. Then deubiquitinase (DUBs) activity associated with the 19S proteasome was determined by using the purified 26S proteasome. As a control, purified 20S proteasome showed no DUBs activity (FIG. 10D). In comparison, the purified 26S proteasome showed 3-fold DUBs activity, which was suppressed when incubated with Gal (FIG. 10D). When this experiment was repeated, it was shown that Gal inhibited DUBs activity of the purified 26S proteasome in a dose-dependent fashion; Gal at a low dose (10 μM) could efficiently inhibit DUBs activity (FIG. 10E).

It was next determined whether DUBs activity could be inhibited in cultured CRPC cells after Gal treatment. As shown in FIG. 11A, DUBs activity was inhibited by Gal at as early as 2 h after Gal treatment. Sustained DUBs inhibition was detected for up to 48 h (FIG. 11A). The levels of proteasomal CT-like activities were inhibited in a time-dependent fashion, but later than DUBs inhibition (FIG. 11B). Oxidized proteins were accumulated by Gal treatment before 2 h, and sustained accumulation was detected up to 72 h (FIG. 11C, a). AR-V7 protein level remained subtle changes up to 56 h and decreased after 64-68 h, and completely depleted after 72 h (FIG. 11C, c). Caspase-3 activity was increased after 24 h treatment with Gal and reached to 5-fold activation after 48 h (FIG. 11D). Consistently, caspase-3-specific cleavage fragments, 89 kD fragment of PARP (PARP/p89) were also detected between 48 and 72 h (FIG. 11C, d). Calpain activation is associated with self-autolysis of its small subunit. A cleaved fragment (28 kD) of calpain small subunit (Cal Sm/p28) was detected during 48-72 h treatment with Gal (FIG. 11C, e). The above results suggest that Gal is an inhibitor of DUBs associated with the 19S proteasomes in CRPC cells. This finding has important clinical significance.

Figure 12A:
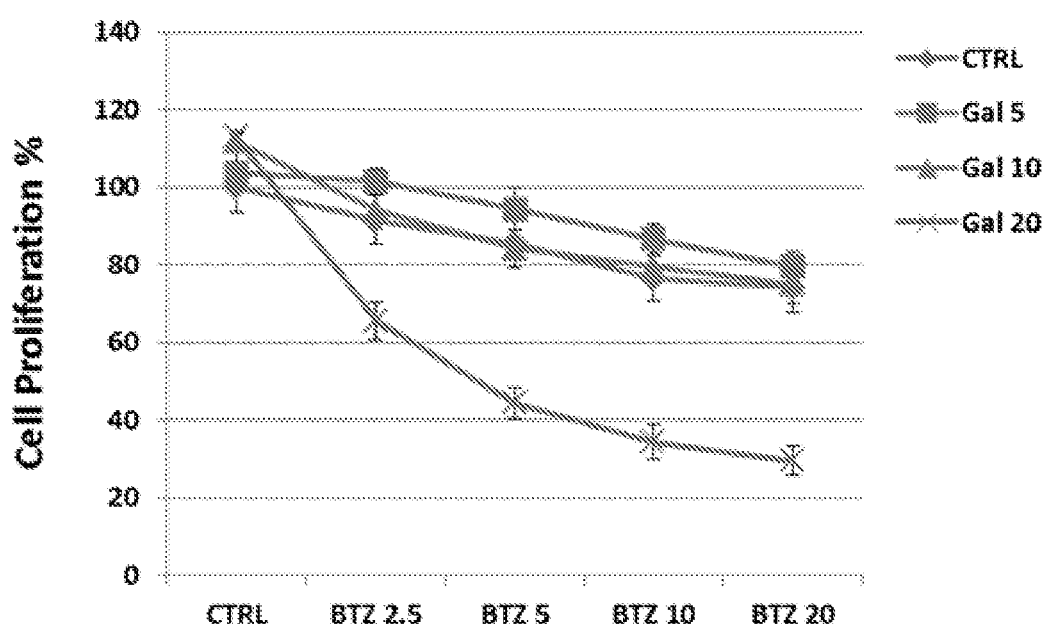
Figure 12B:
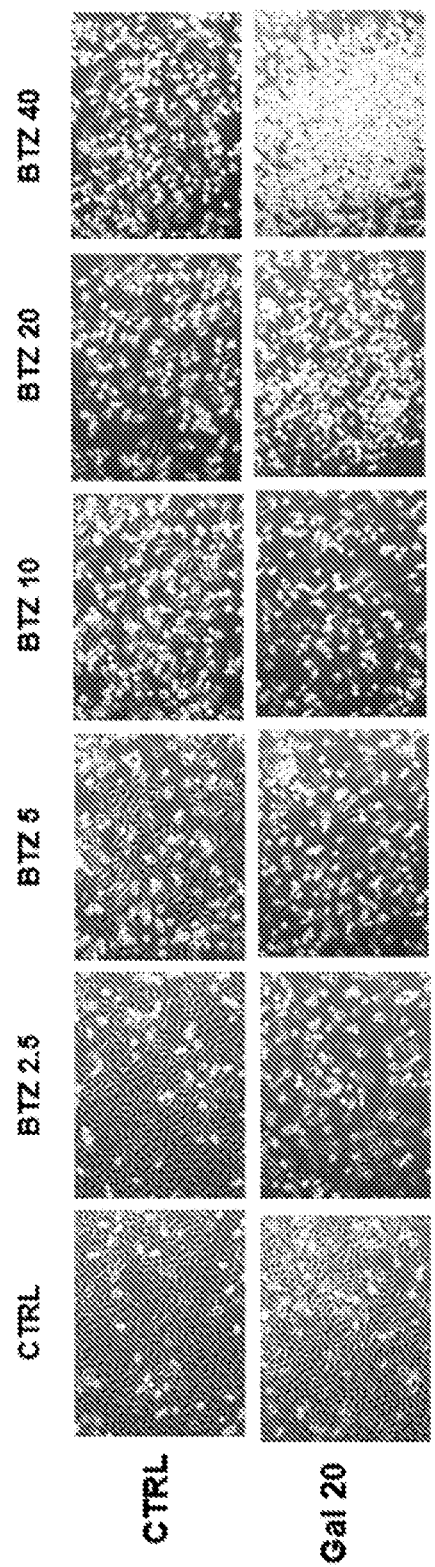
Figure 12C:
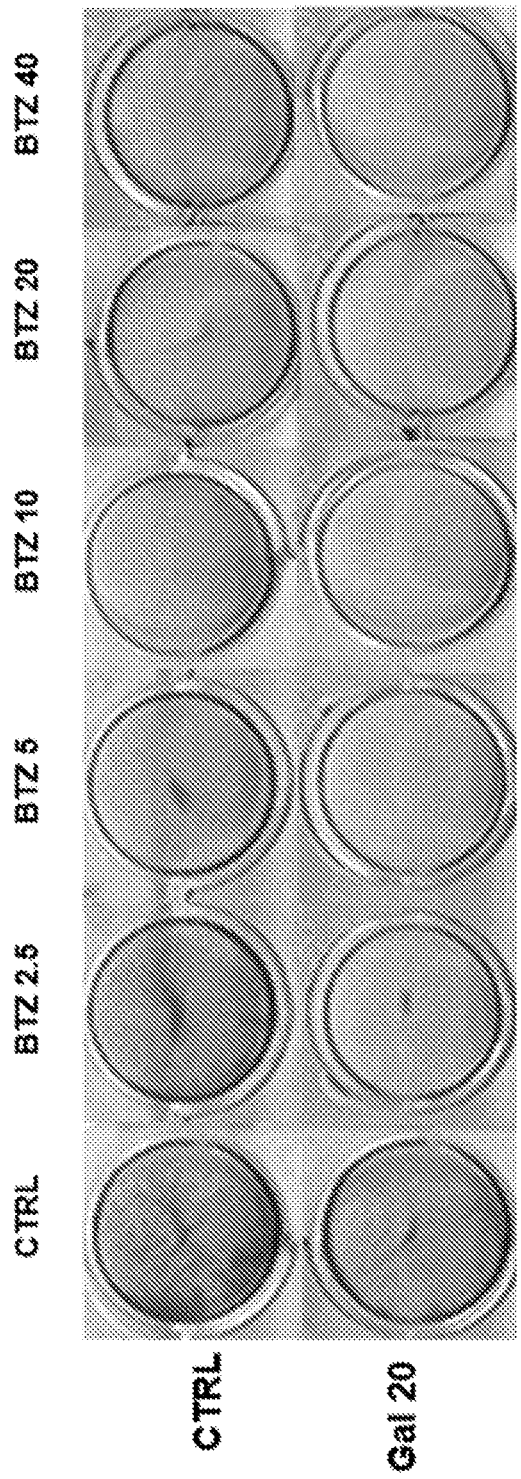
Figure 12D:
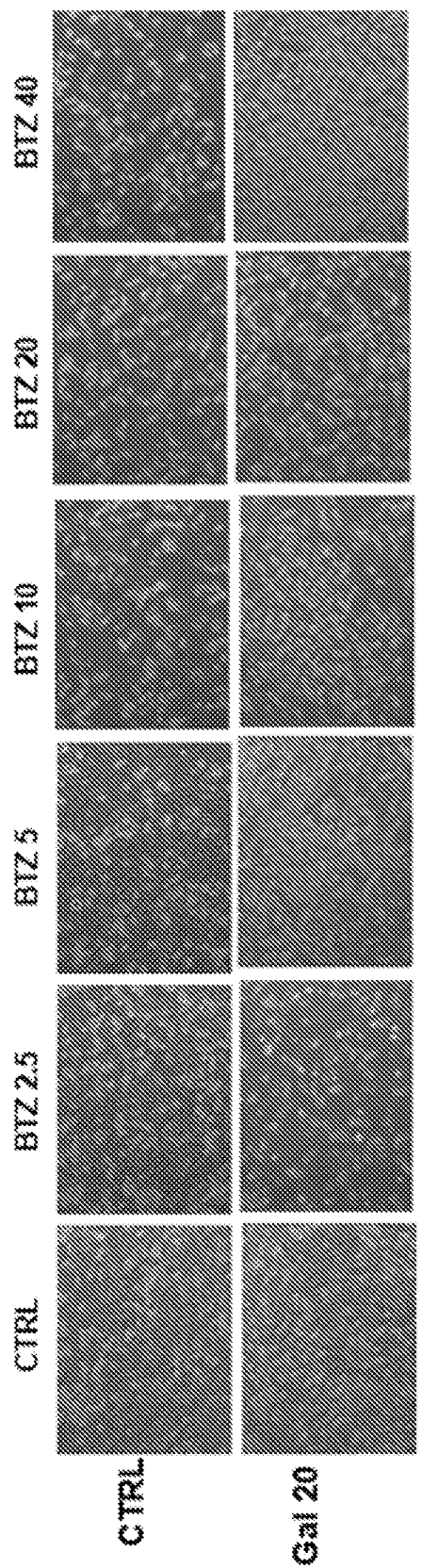
Figure 12E:
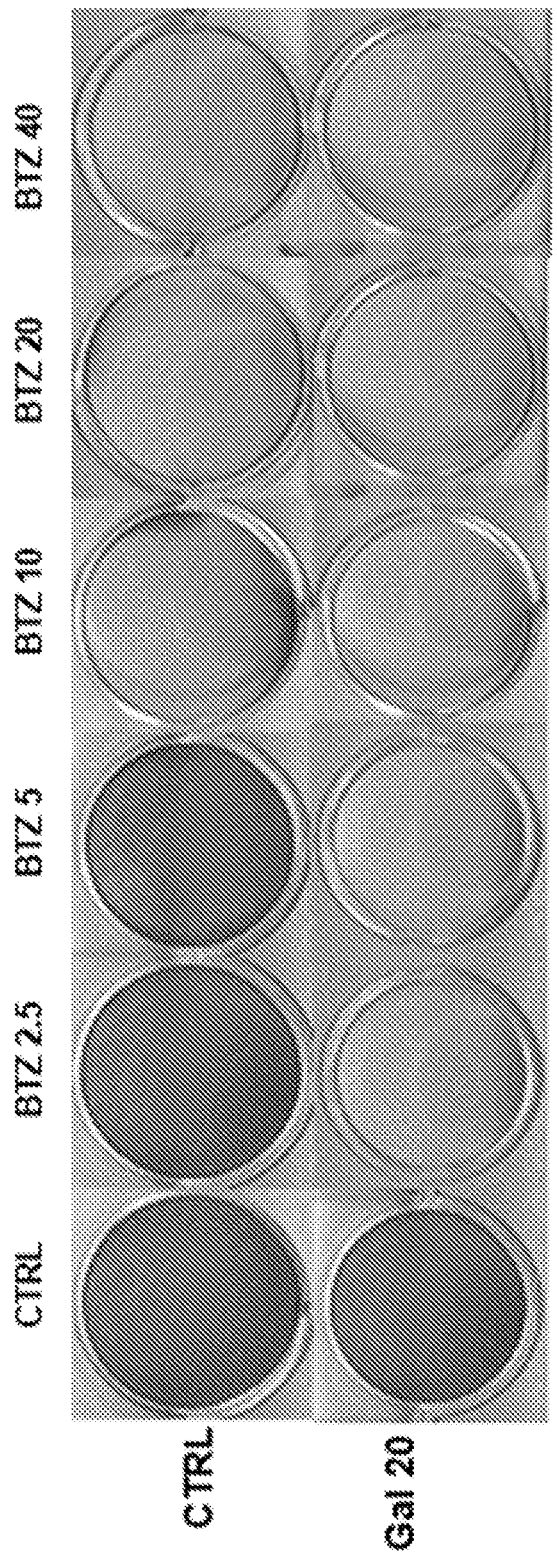

It was next determined if the combinational treatment of Gal and BTZ would induce greater growth inhibition and cell death in CRPC cells. Gal treatment alone for 24 h did not inhibit cell proliferation in 22Rv1 cells. In the presence of bortezomib, cell growth was greatly inhibited by Gal at 20 μM (MTT assay; FIG. 12A). Gal at 20 μM in combination with bortezomib 5 or 10 nM generated greater inhibitory effects on cell proliferation compared to each drug alone (FIG. 12A). Consistently, Bortezomib in combination with Gal induced greater morphological changes (indicator of cell death) as shown by more detached cells or apoptotic cells in co-treatment compared to each drug alone (FIGS. 12B and 12D for 24 and 48 h, respectively). Synergistic effects of Gal in combination with bortezomib were shown. After 24 h (FIG. 12B) and 48 h (FIG. 12D) treatment, bortezomib (2.5 or 5 nM) or Gal alone did not cause apparent morphological changes, but their combination caused apparent or complete cell death. These synergistic effects were reflected in violet staining, showing less staining cells in the combination compared to each drug alone (FIGS. 12C and 12E for 24 and 48 h, respectively).

The combination of Gal and BTZ causes greater proteasome inhibition, more AR-V7 depletion and more CRPC cell death, compared to each drug alone. It was then determined whether Gal could sensitize BTZ-resistant multiple myeloma cells. BTZ-resistant MM cells were sensitive to Gal treatment alone at 10 or 20 μM (FIG. 13A-B); Combination of Gal and BTZ showed greater inhibition on BTZ-resistant MM cells than each drug alone in both Gal dose- and BTZ dose-dependent manners, as evident in two independent experiments (FIG. 13A-B). Next we determined whether Gal and BTZ combination could increase higher levels of cell death in the resistant MM cells. 8826-7BR is a multiple myeloma cell line developed resistance to bortezomib. Gal in combination with bortezomib induced more cell death as shown by stronger cleaved PARP bands generated by cotreatment (FIG. 13C, lanes 7-10) compared with each alone (lane 2 or lanes 3-6). Therefore, Gal is able to overcome bortezomib resistance in MM. This finding has high translational potential to clinics.

In brief, the disclosed studies indicate that Gal acts as an inhibitor of the 19S proteasome-associated DUBs, which can be used to overcome the resistance of 20S inhibitor BTZ for the treatment of MM and other liquid tumors.

As will be understood by one of ordinary skill in the art, while exemplary sequences of proteins described herein are provided, additional homologous and/or variant sequences can be obtained from publicly available databases. Such sequences are included within the teachings of the current disclosure. Homologous sequences are those with shared ancestry. Shared ancestry can occur based on a speciation event (orthologs) or a duplication event (paralogs). Variant sequences include sequences having one or more amino acid additions, deletions, stop positions, or substitutions, as compared to a protein sequence disclosed elsewhere herein. Variants can include allelic forms, representing minor changes in amino acid composition. Homologous sequences and variant sequences will typically exhibit the same qualitative biological activity and elicit a substantially similar response as reference proteins provided herein. Screening of homologues and variants can be performed using assays described elsewhere herein.

Homologous sequences and variant sequences included within the scope of the disclosure can have at least 80% sequence identity; at least 85% sequence identity; at least 90% sequence identity; at least 95% sequence identity or at least 99% sequence identity with an exemplary reference sequence disclosed herein. "Percent (%) amino acid sequence identity" with respect to the sequences identified herein is defined as the percentage of amino acid residues in a candidate sequence that are identical with the amino acid residues in the reference sequence after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, or ALIGN-2. Those skilled in the art can determine appropriate parameters for measuring alignment, including any algorithms needed to achieve maximal alignment over the full-length of the sequences being compared.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in a combination therapy's ability to cause an anti-CRPC or MM effect or to detect 53 kDa and 41 kDa AR-V7 fragments in a blood sample from a subject.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

REFERENCES

1. Ezzell et al., Current oncology reports 2013 June; 15(3):239-48.
2. Tran et al., Science 2009 May 8; 324(5928):787-90.
3. Deshmukh et al., Expert Opin Pharmacother. 2014 January; 15(1):11-22.
4. Antonarakis et al., N Engl J Med. 2014 Sep. 11; 371(11):1028-38.
5. Njar & Brodie, J Med Chem. 2015 Mar. 12; 58(5):2077-87.
6. Taplin et al., ARMOR2: Galeterone in progressive CRPC patients who have failed primary therapy. GU-ASCO-2014, Poster #012914
7. Taplin et al., Activity of galeterone in castrate-resistant Prostate cancer (CRPC) with C-terminal AR Loss: Results from ARMOR2. 26th EORTC-NCI-AACR Symposium on Molecular Targets and Cancer Therapeutics, 18-24 Nov. 2014, Barcelona, Spain
8. Purushottamachar et al., J Med Chem. 2013 Jun. 27; 56(12):4880-98.
9. Kwegyir-Afful et al., Galeterone and VNPT55 induce proteasomal degradation of AR/AR-V7, induce significant apoptosis via cytochrome c release and suppress growth of castration resistant prostate cancer xenografts in vivo. Oncotarget. 2015 Jul. 14.
10. Tsubuki et al., J Biochem. 1996 March; 119(3):572-6.
11. Banerjee & Liefshitz, Anticancer Res. 2001 November-December; 21(6A):3941-7.
12. Yang et al., Cancer Res. 2006 May 1; 66(9):4758-65.
13. Yang et al., J Cell Physiol. 2008 December; 217(3):569-76.
14. Hu et al., Cancer Res. 2009 Jan. 1; 69(1):16-22.
15. Guo et al., Cancer Res. 2009 Mar. 15; 69(6):2305-13.
16. Zhang et al., Apoptosis. 2009 November; 14(11):1289-98.
17. Gao et al., J Cell Biochem. 2000 Sep. 18; 80(1):53-72.
18. Pörn-Ares et al., Cell Death Differ. 1998 December; 5(12):1028-33.
19. Pink et al., Exp Cell Res. 2000 Mar. 15; 255(2):144-55.
20. Chen et al., Curr Cancer Drug Targets. 2011 March; 11(3):239-53. Review.
21. Chen et al., Cancer Res. 2007 Feb. 15; 67(4):1636-44.
22. Yang et al., Mol Pharmacol. 2007 February; 71(2):426-37.
23. Yang et al., J Cell Biochem. 2008 Jan. 1; 103(1):234-44.
24. Yang et al., Int J Cancer. 2009 May 15; 124(10):2450-9.
25. Frezza et al., J Cell Physiol. 2011 November; 226(11):2731-9.
26. Chen et al., Cancer Res. 2007 Oct. 1; 67(19):9258-65.
27. Shen et al., Journal of Cellular Physiology (Rapid Communications), 2014 June; 229(6):688-95.
28. Bizat et al., J Neurosci. 2003 Jun. 15; 23(12):5020-30. Erratum in: J Neurosci. 2003 Oct. 29; 23(30):9960.
29. Huang et al., J Biol Chem. 2013 Apr. 26; 288(17):12161-74.
30. Wei et al., Biochem Pharmacol. 2011 Aug. 15; 82(4):418-25.
31. Wang, Trends Neurosci. 2000 January; 23(1):20-6. Review. Erratum in: Trends Neurosci 2000 February; 23(2):59.
32. Smith et al., Cardiovasc Res. 2012 Oct. 1; 96(1):32-7.
33. Dou et al., Cancer Res. 1993 Apr. 1; 53(7):1493-7.
34. Gong et al., Endocrinology. 2012 December; 153(12):5716-25.
35. Pelley et al., Cancer Res. 2006 Dec. 15; 66(24):11754-62.
36. Cuerrier et al., J. Biol. Chem. 280 (49): 40632-41.
37. Lu et al., Transl Androl Urol. 2013 September; 2(3):178-186.
38. Wellington et al., J Biol Chem. 1998 Apr. 10; 273(15):9158-67.
39. van der Steen et al., Int J Mol Sci. 2013 Jul. 16; 14(7):14833-59.
40. Cai et al., Cancer Res. 2009 Aug. 1; 69(15):6027-32.
41. Martin et al., Endocrinology. 2002 January; 143(1):263-75.
42. Polin et al., Invest New Drugs, 15: 99108, 1997. PMID: 9220288
43. Spade et al., Toxicol Sci. 2014 March; 138(1):148-60.
44. National Research Council. Guide for the Care and Use of Laboratory Animals: Eighth Edition. Washington, D.C.: The National Academies Press, 2011
45. Chen et al., PLoS One. 2012; 7(10):e47186.
46. Kelton et al., Blood. 1992 Nov. 1; 80(9):2246-51.
47. Kim et al., Bioinformatics 27, 1660-1666, 2011.
48. Kim et al., Annals of Applied Statistics 8:1209-1231, 2014.
49. Matsudaira et al., J Biol Chem. 1987 Jul. 25; 262(21):10035-8.
50. Yamashita et al., Neoplasia. 2012 January; 14(1):74-83.
51. Fattman et al., 2001 May 24; 20(23):2918-26.
52. An et al., Cancer Res. 1996 Feb. 1; 56(3):438-42.
53. Fattman et al., J Cell Biochem. 1997 Dec. 1; 67(3):399-408.
54. Zuo et al., J Cell Biochem. 2012 August; 113(8):2567-75.
55. Dou et al., Curr Cancer Drug Targets. 2014; 14(6):517-36. Review.
56. Buac et al., Neoplasia. 2013 December; 15(12):1379-90.
57. Liu et al., Sci Rep. 2014 Jun. 10; 4:5240.
58. Williams et al., Pharm Res. 2013 September; 30(9):2279-89.
59. Huang et al., Cell Res. 2010 December; 20(12):1372-85.
60. Deshmukh et al., Breast Cancer Res Treat. 2015 August; 153(1):79-88.

61. June et al., Curr Protoc Cytom. 2001 May; Chapter 9:Unit 9.8.
62. Gil-Parrado et al., J Biol Chem. 2002 Jul. 26; 277(30): 27217-26.
63. Tsien, Nature 1981, 290(5806):527-528.
64. Tang et al., Biochemical pharmacology 2007, 74(11): 1596-1607.
65. Huang et al., Toxicol Lett. 2014 Aug. 4; 228(3):170-8.
66. Guo Z et al., Cancer Res. 2009 Mar. 15; 69(6): 2305-2313

What is claimed is:

1. A method of monitoring an anti-cancer effect of a castration-resistant prostate cancer (CRPC) therapeutic composition comprising Galeterone and a 20S proteasome inhibitor following its administration to a subject, the method comprising:
    detecting androgen receptor (AR) cleavage product variant 7 (AR-V7), and/or Poly (ADP-ribose) polymerase (PARP) cleavage product p65 (PARP/p65) and/or p89 (PARP/p89), and/or Spectrin α2 cleavage product αII/p120 and/or αII/p150 or 150i in a sample obtained from the subject following the administration,
    wherein presence of the AR cleavage product, and/or the PARP cleavage product, and/or the Spectrin α2 cleavage product is indicative of the anti-cancer effect.

2. The method of claim 1, comprising detecting the AR cleavage product AR-V7.

3. The method of claim 2 wherein the AR-V7 cleavage product is a 53 kDa or a 41 kDa AR-V7 fragment.

4. The method of claim 1, comprising detecting the PARP cleavage product PARP/p65 and/or PARP/p89.

5. The method of claim 1, comprising detecting the Spectrin α2 cleavage product Spectrin aII/p120 and/or Spectrin aII/p150 or 150i.

6. The method of claim 1, wherein detecting the AR cleavage product, and/or the PARP cleavage product, and/or the Spectrin α2 cleavage product in a sample obtained from the subject comprises measuring an activity of one or more 20S proteasome inhibitor(s) or 19S proteasome-associated deubiquitinating enzyme (DUB) inhibitor(s) in a blood sample from the subject.

7. The method of claim 6, wherein the 19S proteasome-associated DUB inhibitor is Galeterone.

8. The method of claim 6, wherein the 20S proteasome inhibitor is selected from β-lapachone, bortezomib, bortesamide, carfilzomib, CEP-18770, disulfiram, epigallocatechin-3-gallate, epoxomicin, lactacystin, laxomib (MLN9708), MG132, MLN9708, oprozomib (ONX 0912), salinosporamide A (NPI-0052, marizomib), or an immunoproteasome inhibitor.

9. The method of claim 8, wherein the 20S proteasome inhibitor is bortezomib.

10. The method of claim 1, wherein the 20S proteasome inhibitor is bortezomib.

11. The method of claim 3, wherein the AR-V7 cleavage product is 53 kDa AR-V7 fragment.

12. The method of claim 2, wherein detecting an AR-V7 cleavage product comprises contacting the biological sample with an AR-V7-specific monoclonal antibody.

13. The method of claim 1, further comprising using the indication of the anti-cancer effect to monitor CRPC treatment efficacy.

14. A method of monitoring an anti-cancer effect of a combination therapy comprising Galeterone and a 20S proteasome inhibitor following its administration to a subject, the method comprising:

obtaining a biological sample from a subject following the administration;

contacting the biological sample with at least one antibody specific for androgen receptor (AR), Poly (ADP-ribose) polymerase (PARP), or Spectrin α2;

detecting the binding of the at least one antibody to AR cleavage product variant 7 (AR-V7), PARP cleavage product p65 (PARP/p65) and/or p89 (PARP/p89), or Spectrin α2 cleavage product aII/p120 and/or aII/p150 or 150i in the biological sample, wherein detection of at least one of the AR cleavage product, the PARP cleavage product, or the Spectrin α2 cleavage product is indicative of the anti-cancer effect.

15. The method of claim 14, wherein the at least one antibody is an AR-V7-specific monoclonal antibody, and the method comprises detecting binding of the antibody to a 53 kDa AR-V7 fragment or a 41 kDa AR-V7 fragment.

16. The method of claim 15, wherein the method comprises detecting binding of the antibody to a 53 kDa AR-V7 fragment.

17. The method of claim 8, the immunoproteasome inhibitor is selected from UK-101, IPSI-001, YU-102, ONX 0914, and PR-924 (IPSI).

* * * * *

SEQUENCE LISTING

```
<160> NUMBER OF SEQ ID NOS: 4

<210> SEQ ID NO 1
<211> LENGTH: 917
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Glu Thr Ser
65                  70                  75                  80

Pro Arg Gln Gln Gln Gln Gln Gly Glu Asp Gly Ser Pro Gln Ala
                85                  90                  95

His Arg Arg Gly Pro Thr Gly Tyr Leu Val Leu Asp Glu Glu Gln Gln
                100                 105                 110

Pro Ser Gln Pro Gln Ser Ala Leu Glu Cys His Pro Glu Arg Gly Cys
            115                 120                 125

Val Pro Glu Pro Gly Ala Ala Val Ala Ala Ser Lys Gly Leu Pro Gln
130                 135                 140

Gln Leu Pro Ala Pro Pro Asp Glu Asp Asp Ser Ala Ala Pro Ser Thr
145                 150                 155                 160

Leu Ser Leu Leu Gly Pro Thr Phe Pro Gly Leu Ser Ser Cys Ser Ala
                165                 170                 175

Asp Leu Lys Asp Ile Leu Ser Glu Ala Ser Thr Met Gln Leu Leu Gln
            180                 185                 190

Gln Gln Gln Gln Glu Ala Val Ser Glu Gly Ser Ser Ser Gly Arg Ala
        195                 200                 205

Arg Glu Arg Ser Gly Ala Pro Thr Ser Ser Lys Asp Asn Tyr Leu Gly
    210                 215                 220

Gly Thr Ser Thr Ile Ser Asp Asn Ala Lys Glu Leu Cys Lys Ala Val
225                 230                 235                 240

Ser Val Ser Met Gly Leu Gly Val Glu Ala Leu Glu His Leu Ser Pro
                245                 250                 255

Gly Glu Gln Leu Arg Gly Asp Cys Met Tyr Ala Pro Leu Leu Gly Val
            260                 265                 270

Pro Pro Ala Val Arg Pro Thr Pro Cys Ala Pro Leu Ala Glu Cys Lys
        275                 280                 285

Gly Ser Leu Leu Asp Asp Ser Ala Gly Lys Ser Thr Glu Asp Thr Ala
    290                 295                 300

Glu Tyr Ser Pro Phe Lys Gly Gly Tyr Thr Lys Gly Leu Glu Gly Glu
305                 310                 315                 320

Ser Leu Gly Cys Ser Gly Ser Ala Ala Ala Gly Ser Ser Gly Thr Leu
                325                 330                 335
```

-continued

```
Glu Leu Pro Ser Thr Leu Ser Leu Tyr Lys Ser Gly Ala Leu Asp Glu
                340                 345                 350

Ala Ala Ala Tyr Gln Ser Arg Asp Tyr Tyr Asn Phe Pro Leu Ala Leu
            355                 360                 365

Ala Gly Pro Pro Pro Pro Pro Pro Pro His Pro His Ala Arg Ile
        370                 375                 380

Lys Leu Glu Asn Pro Leu Asp Tyr Gly Ser Ala Trp Ala Ala Ala
385                 390                 395                 400

Ala Gln Cys Arg Tyr Gly Asp Leu Ala Ser Leu His Gly Ala Gly Ala
            405                 410                 415

Ala Gly Pro Gly Ser Gly Ser Pro Ser Ala Ala Ser Ser Ser Trp
        420                 425                 430

His Thr Leu Phe Thr Ala Glu Glu Gly Gln Leu Tyr Gly Pro Cys Gly
            435                 440                 445

Gly Gly Gly Gly Gly Gly Gly Gly Gly Gly Gly Gly Gly Gly
        450                 455                 460

Gly Gly Gly Gly Gly Gly Glu Ala Gly Ala Val Ala Pro Tyr Gly Tyr
465                 470                 475                 480

Thr Arg Pro Pro Gln Gly Leu Ala Gly Gln Glu Ser Asp Phe Thr Ala
                485                 490                 495

Pro Asp Val Trp Tyr Pro Gly Gly Met Val Ser Arg Val Pro Tyr Pro
            500                 505                 510

Ser Pro Thr Cys Val Lys Ser Glu Met Gly Pro Trp Met Asp Ser Tyr
            515                 520                 525

Ser Gly Pro Tyr Gly Asp Met Arg Leu Glu Thr Ala Arg Asp His Val
        530                 535                 540

Leu Pro Ile Asp Tyr Tyr Phe Pro Pro Gln Lys Thr Cys Leu Ile Cys
545                 550                 555                 560

Gly Asp Glu Ala Ser Gly Cys His Tyr Gly Ala Leu Thr Cys Gly Ser
                565                 570                 575

Cys Lys Val Phe Phe Lys Arg Ala Ala Glu Gly Lys Gln Lys Tyr Leu
            580                 585                 590

Cys Ala Ser Arg Asn Asp Cys Thr Ile Asp Lys Phe Arg Arg Lys Asn
            595                 600                 605

Cys Pro Ser Cys Arg Leu Arg Lys Cys Tyr Glu Ala Gly Met Thr Leu
        610                 615                 620

Gly Ala Arg Lys Leu Lys Lys Leu Gly Asn Leu Lys Leu Gln Glu Glu
625                 630                 635                 640

Gly Glu Ala Ser Ser Thr Thr Ser Pro Thr Glu Glu Thr Thr Gln Lys
                645                 650                 655

Leu Thr Val Ser His Ile Glu Gly Tyr Glu Cys Gln Pro Ile Phe Leu
            660                 665                 670

Asn Val Leu Glu Ala Ile Glu Pro Gly Val Val Cys Ala Gly His Asp
        675                 680                 685

Asn Asn Gln Pro Asp Ser Phe Ala Ala Leu Leu Ser Ser Leu Asn Glu
        690                 695                 700

Leu Gly Glu Arg Gln Leu Val His Val Val Lys Trp Ala Lys Ala Leu
705                 710                 715                 720

Pro Gly Phe Arg Asn Leu His Val Asp Asp Gln Met Ala Val Ile Gln
                725                 730                 735

Tyr Ser Trp Met Gly Leu Met Val Phe Ala Met Gly Trp Arg Ser Phe
            740                 745                 750
```

-continued

```
Thr Asn Val Asn Ser Arg Met Leu Tyr Phe Ala Pro Asp Leu Val Phe
            755                 760                 765

Asn Glu Tyr Arg Met His Lys Ser Arg Met Tyr Ser Gln Cys Val Arg
770                 775                 780

Met Arg His Leu Ser Gln Glu Phe Gly Trp Leu Gln Ile Thr Pro Gln
785                 790                 795                 800

Glu Phe Leu Cys Met Lys Ala Leu Leu Leu Phe Ser Ile Ile Pro Val
                805                 810                 815

Asp Gly Leu Lys Asn Gln Lys Phe Phe Asp Glu Leu Arg Met Asn Tyr
            820                 825                 830

Ile Lys Glu Leu Asp Arg Ile Ile Ala Cys Lys Arg Lys Asn Pro Thr
835                 840                 845

Ser Cys Ser Arg Arg Phe Tyr Gln Leu Thr Lys Leu Leu Asp Ser Val
850                 855                 860

Gln Pro Ile Ala Arg Glu Leu His Gln Phe Thr Phe Asp Leu Leu Ile
865                 870                 875                 880

Lys Ser His Met Val Ser Val Asp Phe Pro Glu Met Met Ala Glu Ile
                885                 890                 895

Ile Ser Val Gln Val Pro Lys Ile Leu Ser Gly Lys Val Lys Pro Ile
                900                 905                 910

Tyr Phe His Thr Gln
            915

<210> SEQ ID NO 2
<211> LENGTH: 645
<212> TYPE: PRT
<213> ORGANISM: Homo sapiens

<400> SEQUENCE: 2

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Glu Thr Ser Pro Arg Gln Gln Gln Gln Gln Gln
                85                  90                  95

Gly Glu Asp Gly Ser Pro Gln Ala His Arg Arg Gly Pro Thr Gly Tyr
            100                 105                 110

Leu Val Leu Asp Glu Glu Gln Gln Pro Ser Gln Pro Gln Ser Ala Leu
        115                 120                 125

Glu Cys His Pro Glu Arg Gly Cys Val Pro Glu Pro Gly Ala Ala Val
    130                 135                 140

Ala Ala Ser Lys Gly Leu Pro Gln Gln Leu Pro Ala Pro Pro Asp Glu
145                 150                 155                 160

Asp Asp Ser Ala Ala Pro Ser Thr Leu Ser Leu Leu Gly Pro Thr Phe
                165                 170                 175

Pro Gly Leu Ser Ser Cys Ser Ala Asp Leu Lys Asp Ile Leu Ser Glu
            180                 185                 190

Ala Ser Thr Met Gln Leu Leu Gln Gln Gln Gln Glu Ala Val Ser
        195                 200                 205
```

```
Glu Gly Ser Ser Ser Gly Arg Ala Arg Glu Ala Ser Gly Ala Pro Thr
    210             215                 220

Ser Ser Lys Asp Asn Tyr Leu Gly Gly Thr Ser Thr Ile Ser Asp Asn
225             230                 235                 240

Ala Lys Glu Leu Cys Lys Ala Val Ser Val Ser Met Gly Leu Gly Val
                245                 250                 255

Glu Ala Leu Glu His Leu Ser Pro Gly Glu Gln Leu Arg Gly Asp Cys
            260                 265                 270

Met Tyr Ala Pro Leu Leu Gly Val Pro Pro Ala Val Arg Pro Thr Pro
        275                 280                 285

Cys Ala Pro Leu Ala Glu Cys Lys Gly Ser Leu Leu Asp Asp Ser Ala
    290                 295                 300

Gly Lys Ser Thr Glu Asp Thr Ala Glu Tyr Ser Pro Phe Lys Gly Gly
305             310                 315                 320

Tyr Thr Lys Gly Leu Glu Gly Glu Ser Leu Gly Cys Ser Gly Ser Ala
                325                 330                 335

Ala Ala Gly Ser Ser Gly Thr Leu Glu Leu Pro Ser Thr Leu Ser Leu
            340                 345                 350

Tyr Lys Ser Gly Ala Leu Asp Glu Ala Ala Tyr Gln Ser Arg Asp
        355                 360                 365

Tyr Tyr Asn Phe Pro Leu Ala Leu Ala Gly Pro Pro Pro Pro Pro
    370                 375                 380

Pro Pro His Pro His Ala Arg Ile Lys Leu Glu Asn Pro Leu Asp Tyr
385             390                 395                 400

Gly Ser Ala Trp Ala Ala Ala Ala Gln Cys Arg Tyr Gly Asp Leu
                405                 410                 415

Ala Ser Leu His Gly Ala Gly Ala Gly Pro Gly Ser Gly Ser Pro
            420                 425                 430

Ser Ala Ala Ala Ser Ser Ser Trp His Thr Leu Phe Thr Ala Glu Glu
    435                 440                 445

Gly Gln Leu Tyr Gly Pro Cys Gly Gly Gly Gly Gly Gly Gly Gly
    450                 455                 460

Gly Gly Gly Gly Gly Gly Gly Gly Gly Glu Ala Gly Ala Val Ala
465                 470                 475                 480

Pro Tyr Gly Tyr Thr Arg Pro Pro Gln Gly Leu Ala Gly Gln Glu Ser
                485                 490                 495

Asp Phe Thr Ala Pro Asp Val Trp Tyr Pro Gly Gly Met Val Ser Arg
            500                 505                 510

Val Pro Tyr Pro Ser Pro Thr Cys Val Lys Ser Glu Met Gly Pro Trp
        515                 520                 525

Met Asp Ser Tyr Ser Gly Pro Tyr Gly Asp Met Arg Leu Glu Thr Ala
    530                 535                 540

Arg Asp His Val Leu Pro Ile Asp Tyr Tyr Phe Pro Pro Gln Lys Thr
545             550                 555                 560

Cys Leu Ile Cys Gly Asp Glu Ala Ser Gly Cys His Tyr Gly Ala Leu
                565                 570                 575

Thr Cys Gly Ser Cys Lys Val Phe Phe Lys Arg Ala Ala Glu Gly Lys
            580                 585                 590

Gln Lys Tyr Leu Cys Ala Ser Arg Asn Asp Cys Thr Ile Asp Lys Phe
        595                 600                 605

Arg Arg Lys Asn Cys Pro Ser Cys Arg Leu Arg Lys Cys Tyr Glu Ala
    610                 615                 620
```

Gly Met Thr Leu Gly Glu Lys Phe Arg Val Gly Asn Cys Lys His Leu
625                 630                 635                 640

Lys Met Thr Arg Pro
            645

<210> SEQ ID NO 3
<211> LENGTH: 2472
<212> TYPE: PRT
<213> ORGANISM: Homo sapiens

<400> SEQUENCE: 3

Met Asp Pro Ser Gly Val Lys Val Leu Glu Thr Ala Glu Asp Ile Gln
1               5                   10                  15

Glu Arg Arg Gln Gln Val Leu Asp Arg Tyr His Arg Phe Lys Glu Leu
            20                  25                  30

Ser Thr Leu Arg Arg Gln Lys Leu Glu Asp Ser Tyr Arg Phe Gln Phe
        35                  40                  45

Phe Gln Arg Asp Ala Glu Glu Leu Glu Lys Trp Ile Gln Glu Lys Leu
    50                  55                  60

Gln Ile Ala Ser Asp Glu Asn Tyr Lys Asp Pro Thr Asn Leu Gln Gly
65                  70                  75                  80

Lys Leu Gln Lys His Gln Ala Phe Glu Ala Glu Val Gln Ala Asn Ser
                85                  90                  95

Gly Ala Ile Val Lys Leu Asp Glu Thr Gly Asn Leu Met Ile Ser Glu
            100                 105                 110

Gly His Phe Ala Ser Glu Thr Ile Arg Thr Arg Leu Met Glu Leu His
        115                 120                 125

Arg Gln Trp Glu Leu Leu Leu Glu Lys Met Arg Glu Lys Gly Ile Lys
    130                 135                 140

Leu Leu Gln Ala Gln Lys Leu Val Gln Tyr Leu Arg Glu Cys Glu Asp
145                 150                 155                 160

Val Met Asp Trp Ile Asn Asp Lys Glu Ala Ile Val Thr Ser Glu Glu
                165                 170                 175

Leu Gly Gln Asp Leu Glu His Val Glu Val Leu Gln Lys Lys Phe Glu
            180                 185                 190

Glu Phe Gln Thr Asp Met Ala Ala His Glu Glu Arg Val Asn Glu Val
        195                 200                 205

Asn Gln Phe Ala Ala Lys Leu Ile Gln Glu Gln His Pro Glu Glu Glu
    210                 215                 220

Leu Ile Lys Thr Lys Gln Asp Glu Val Asn Ala Ala Trp Gln Arg Leu
225                 230                 235                 240

Lys Gly Leu Ala Leu Gln Arg Gln Gly Lys Leu Phe Gly Ala Ala Glu
                245                 250                 255

Val Gln Arg Phe Asn Arg Asp Val Asp Glu Thr Ile Ser Trp Ile Lys
            260                 265                 270

Glu Lys Glu Gln Leu Met Ala Ser Asp Asp Phe Gly Arg Asp Leu Ala
        275                 280                 285

Ser Val Gln Ala Leu Leu Arg Lys His Glu Gly Leu Glu Arg Asp Leu
    290                 295                 300

Ala Ala Leu Glu Asp Lys Val Lys Ala Leu Cys Ala Glu Ala Asp Arg
305                 310                 315                 320

Leu Gln Gln Ser His Pro Leu Ser Ala Thr Gln Ile Gln Val Lys Arg
                325                 330                 335

Glu Glu Leu Ile Thr Asn Trp Glu Gln Ile Arg Thr Leu Ala Ala Glu
            340                 345                 350

```
Arg His Ala Arg Leu Asn Asp Ser Tyr Arg Leu Gln Arg Phe Leu Ala
            355                 360                 365
Asp Phe Arg Asp Leu Thr Ser Trp Val Thr Glu Met Lys Ala Leu Ile
        370                 375                 380
Asn Ala Asp Glu Leu Ala Ser Asp Val Ala Gly Ala Glu Ala Leu Leu
385                 390                 395                 400
Asp Arg His Gln Glu His Lys Gly Glu Ile Asp Ala His Glu Asp Ser
                405                 410                 415
Phe Lys Ser Ala Asp Glu Ser Gly Gln Ala Leu Leu Ala Ala Gly His
                420                 425                 430
Tyr Ala Ser Asp Glu Val Arg Glu Lys Leu Thr Val Leu Ser Glu Glu
            435                 440                 445
Arg Ala Ala Leu Leu Glu Leu Trp Glu Leu Arg Arg Gln Gln Tyr Glu
            450                 455                 460
Gln Cys Met Asp Leu Gln Leu Phe Tyr Arg Asp Thr Glu Gln Val Asp
465                 470                 475                 480
Asn Trp Met Ser Lys Gln Glu Ala Phe Leu Leu Asn Glu Asp Leu Gly
                485                 490                 495
Asp Ser Leu Asp Ser Val Glu Ala Leu Leu Lys Lys His Glu Asp Phe
                500                 505                 510
Glu Lys Ser Leu Ser Ala Gln Glu Glu Lys Ile Thr Ala Leu Asp Glu
            515                 520                 525
Phe Ala Thr Lys Leu Ile Gln Asn Asn His Tyr Ala Met Glu Asp Val
            530                 535                 540
Ala Thr Arg Arg Asp Ala Leu Leu Ser Arg Arg Asn Ala Leu His Glu
545                 550                 555                 560
Arg Ala Met Arg Arg Ala Gln Leu Ala Asp Ser Phe His Leu Gln
                565                 570                 575
Gln Phe Phe Arg Asp Ser Asp Glu Leu Lys Ser Trp Val Asn Glu Lys
                580                 585                 590
Met Lys Thr Ala Thr Asp Glu Ala Tyr Lys Asp Pro Ser Asn Leu Gln
            595                 600                 605
Gly Lys Val Gln Lys His Gln Ala Phe Glu Ala Glu Leu Ser Ala Asn
            610                 615                 620
Gln Ser Arg Ile Asp Ala Leu Glu Lys Ala Gly Gln Lys Leu Ile Asp
625                 630                 635                 640
Val Asn His Tyr Ala Lys Asp Glu Val Ala Ala Arg Met Asn Glu Val
                645                 650                 655
Ile Ser Leu Trp Lys Lys Leu Leu Glu Ala Thr Glu Leu Lys Gly Ile
                660                 665                 670
Lys Leu Arg Glu Ala Asn Gln Gln Gln Gln Phe Asn Arg Asn Val Glu
            675                 680                 685
Asp Ile Glu Leu Trp Leu Tyr Glu Val Glu Gly His Leu Ala Ser Asp
            690                 695                 700
Asp Tyr Gly Lys Asp Leu Thr Asn Val Gln Asn Leu Gln Lys Lys His
705                 710                 715                 720
Ala Leu Leu Glu Ala Asp Val Ala Ala His Gln Asp Arg Ile Asp Gly
                725                 730                 735
Ile Thr Ile Gln Ala Arg Gln Phe Gln Asp Ala Gly His Phe Asp Ala
            740                 745                 750
Glu Asn Ile Lys Lys Lys Gln Glu Ala Leu Val Ala Arg Tyr Glu Ala
            755                 760                 765
```

```
Leu Lys Glu Pro Met Val Ala Arg Lys Gln Lys Leu Ala Asp Ser Leu
770                 775                 780

Arg Leu Gln Gln Leu Phe Arg Asp Val Glu Asp Glu Glu Thr Trp Ile
785                 790                 795                 800

Arg Glu Lys Glu Pro Ile Ala Ala Ser Thr Asn Arg Gly Lys Asp Leu
                805                 810                 815

Ile Gly Val Gln Asn Leu Leu Lys Lys His Gln Ala Leu Gln Ala Glu
            820                 825                 830

Ile Ala Gly His Glu Pro Arg Ile Lys Ala Val Thr Gln Lys Gly Asn
                835                 840                 845

Ala Met Val Glu Glu Gly His Phe Ala Ala Glu Asp Val Lys Ala Lys
850                 855                 860

Leu His Glu Leu Asn Gln Lys Trp Glu Ala Leu Lys Ala Lys Ala Ser
865                 870                 875                 880

Gln Arg Arg Gln Asp Leu Glu Asp Ser Leu Gln Ala Gln Gln Tyr Phe
                885                 890                 895

Ala Asp Ala Asn Glu Ala Glu Ser Trp Met Arg Glu Lys Glu Pro Ile
            900                 905                 910

Val Gly Ser Thr Asp Tyr Gly Lys Asp Glu Asp Ser Ala Glu Ala Leu
                915                 920                 925

Leu Lys Lys His Glu Ala Leu Met Ser Asp Leu Ser Ala Tyr Gly Ser
930                 935                 940

Ser Ile Gln Ala Leu Arg Glu Gln Ala Gln Ser Cys Arg Gln Gln Val
945                 950                 955                 960

Ala Pro Thr Asp Asp Glu Thr Gly Lys Glu Leu Val Leu Ala Leu Tyr
                965                 970                 975

Asp Tyr Gln Glu Lys Ser Pro Arg Glu Val Thr Met Lys Lys Gly Asp
            980                 985                 990

Ile Leu Thr Leu Leu Asn Ser Thr Asn Lys Asp Trp Trp Lys Val Glu
                995                 1000                1005

Val Asn Asp Arg Gln Gly Phe Val Pro Ala Ala Tyr Val Lys Lys
        1010                1015                1020

Leu Asp Pro Ala Gln Ser Ala Ser Arg Glu Asn Leu Leu Glu Glu
        1025                1030                1035

Gln Gly Ser Ile Ala Leu Arg Gln Glu Gln Ile Asp Asn Gln Thr
        1040                1045                1050

Arg Ile Thr Lys Glu Ala Gly Ser Val Ser Leu Arg Met Lys Gln
        1055                1060                1065

Val Glu Glu Leu Tyr His Ser Leu Leu Glu Leu Gly Glu Lys Arg
        1070                1075                1080

Lys Gly Met Leu Glu Lys Ser Cys Lys Lys Phe Met Leu Phe Arg
        1085                1090                1095

Glu Ala Asn Glu Leu Gln Gln Trp Ile Asn Glu Lys Glu Ala Ala
        1100                1105                1110

Leu Thr Ser Glu Glu Val Gly Ala Asp Leu Glu Gln Val Glu Val
        1115                1120                1125

Leu Gln Lys Lys Phe Asp Asp Phe Gln Lys Asp Leu Lys Ala Asn
        1130                1135                1140

Glu Ser Arg Leu Lys Asp Ile Asn Lys Val Ala Glu Asp Leu Glu
        1145                1150                1155

Ser Glu Gly Leu Met Ala Glu Glu Val Gln Ala Val Gln Gln Gln
        1160                1165                1170
```

```
Glu Val Tyr Gly Met Met Pro Arg Asp Glu Thr Asp Ser Lys Thr
1175                1180                1185

Ala Ser Pro Trp Lys Ser Ala Arg Leu Met Val His Thr Val Ala
1190                1195                1200

Thr Phe Asn Ser Ile Lys Glu Leu Asn Glu Arg Trp Arg Ser Leu
1205                1210                1215

Gln Gln Leu Ala Glu Glu Arg Ser Gln Leu Leu Gly Ser Ala His
1220                1225                1230

Glu Val Gln Arg Phe His Arg Asp Ala Asp Glu Thr Lys Glu Trp
1235                1240                1245

Ile Glu Glu Lys Asn Gln Ala Leu Asn Thr Asp Asn Tyr Gly His
1250                1255                1260

Asp Leu Ala Ser Val Gln Ala Leu Gln Arg Lys His Glu Gly Phe
1265                1270                1275

Glu Arg Asp Leu Ala Ala Leu Gly Asp Lys Val Asn Ser Leu Gly
1280                1285                1290

Glu Thr Ala Glu Arg Leu Ile Gln Ser His Pro Glu Ser Ala Glu
1295                1300                1305

Asp Leu Gln Glu Lys Cys Thr Glu Leu Asn Gln Ala Trp Ser Ser
1310                1315                1320

Leu Gly Lys Arg Ala Asp Gln Arg Lys Ala Lys Leu Gly Asp Ser
1325                1330                1335

His Asp Leu Gln Arg Phe Leu Ser Asp Phe Arg Asp Leu Met Ser
1340                1345                1350

Trp Ile Asn Gly Ile Arg Gly Leu Val Ser Ser Asp Glu Leu Ala
1355                1360                1365

Lys Asp Val Thr Gly Ala Glu Ala Leu Leu Glu Arg His Gln Glu
1370                1375                1380

His Arg Thr Glu Ile Asp Ala Arg Ala Gly Thr Phe Gln Ala Phe
1385                1390                1395

Glu Gln Phe Gly Gln Gln Leu Leu Ala His Gly His Tyr Ala Ser
1400                1405                1410

Pro Glu Ile Lys Gln Lys Leu Asp Ile Leu Asp Gln Glu Arg Ala
1415                1420                1425

Asp Leu Glu Lys Ala Trp Val Gln Arg Arg Met Met Leu Asp Gln
1430                1435                1440

Cys Leu Glu Leu Gln Leu Phe His Arg Asp Cys Glu Gln Ala Glu
1445                1450                1455

Asn Trp Met Ala Ala Arg Glu Ala Phe Leu Asn Thr Glu Asp Lys
1460                1465                1470

Gly Asp Ser Leu Asp Ser Val Glu Ala Leu Ile Lys Lys His Glu
1475                1480                1485

Asp Phe Asp Lys Ala Ile Asn Val Gln Glu Glu Lys Ile Ala Ala
1490                1495                1500

Leu Gln Ala Phe Ala Asp Gln Leu Ile Ala Ala Gly His Tyr Ala
1505                1510                1515

Lys Gly Asp Ile Ser Ser Arg Arg Asn Glu Val Leu Asp Arg Trp
1520                1525                1530

Arg Arg Leu Lys Ala Gln Met Ile Glu Lys Arg Ser Lys Leu Gly
1535                1540                1545

Glu Ser Gln Thr Leu Gln Gln Phe Ser Arg Asp Val Asp Glu Ile
1550                1555                1560
```

-continued

```
Glu Ala Trp Ile Ser Glu Lys Leu Gln Thr Ala Ser Asp Glu Ser
1565                1570                1575

Tyr Lys Asp Pro Thr Asn Ile Gln Ser Lys His Gln Lys His Gln
1580                1585                1590

Ala Phe Glu Ala Glu Leu His Ala Asn Ala Asp Arg Ile Arg Gly
1595                1600                1605

Val Ile Asp Met Gly Asn Ser Leu Ile Glu Arg Gly Ala Cys Ala
1610                1615                1620

Gly Ser Glu Asp Ala Val Lys Ala Arg Leu Ala Ala Leu Ala Asp
1625                1630                1635

Gln Trp Gln Phe Leu Val Gln Lys Ser Ala Glu Lys Ser Gln Lys
1640                1645                1650

Leu Lys Glu Ala Asn Lys Gln Gln Asn Phe Asn Thr Gly Ile Lys
1655                1660                1665

Asp Phe Asp Phe Trp Leu Ser Glu Val Glu Ala Leu Leu Ala Ser
1670                1675                1680

Glu Asp Tyr Gly Lys Asp Leu Ala Ser Val Asn Asn Leu Leu Lys
1685                1690                1695

Lys His Gln Leu Leu Glu Ala Asp Ile Ser Ala His Glu Asp Arg
1700                1705                1710

Leu Lys Asp Leu Asn Ser Gln Ala Asp Ser Leu Met Thr Ser Ser
1715                1720                1725

Ala Phe Asp Thr Ser Gln Val Lys Asp Lys Arg Asp Thr Ile Asn
1730                1735                1740

Gly Arg Phe Gln Lys Ile Lys Ser Met Ala Ala Ser Arg Arg Ala
1745                1750                1755

Lys Leu Asn Glu Ser His Arg Leu His Gln Phe Phe Arg Asp Met
1760                1765                1770

Asp Asp Glu Glu Ser Trp Ile Lys Glu Lys Lys Leu Leu Val Gly
1775                1780                1785

Ser Glu Asp Tyr Gly Arg Asp Leu Thr Gly Val Gln Asn Leu Arg
1790                1795                1800

Lys Lys His Lys Arg Leu Glu Ala Glu Leu Ala Ala His Glu Pro
1805                1810                1815

Ala Ile Gln Gly Val Leu Asp Thr Gly Lys Lys Leu Ser Asp Asp
1820                1825                1830

Asn Thr Ile Gly Lys Glu Glu Ile Gln Gln Arg Leu Ala Gln Phe
1835                1840                1845

Val Glu His Trp Lys Glu Leu Lys Gln Leu Ala Ala Ala Arg Gly
1850                1855                1860

Gln Arg Leu Glu Glu Ser Leu Glu Tyr Gln Gln Phe Val Ala Asn
1865                1870                1875

Val Glu Glu Glu Glu Ala Trp Ile Asn Glu Lys Met Thr Leu Val
1880                1885                1890

Ala Ser Glu Asp Tyr Gly Asp Thr Leu Ala Ala Ile Gln Gly Leu
1895                1900                1905

Leu Lys Lys His Glu Ala Phe Glu Thr Asp Phe Thr Val His Lys
1910                1915                1920

Asp Arg Val Asn Asp Val Cys Thr Asn Gly Gln Asp Leu Ile Lys
1925                1930                1935

Lys Asn Asn His His Glu Glu Asn Ile Ser Ser Lys Met Lys Gly
1940                1945                1950
```

```
Leu Asn Gly Lys Val Ser Asp Leu Glu Lys Ala Ala Ala Gln Arg
1955                1960                1965

Lys Ala Lys Leu Asp Glu Asn Ser Ala Phe Leu Gln Phe Asn Trp
1970                1975                1980

Lys Ala Asp Val Val Glu Ser Trp Ile Gly Glu Lys Glu Asn Ser
1985                1990                1995

Leu Lys Thr Asp Asp Tyr Gly Arg Asp Leu Ser Ser Val Gln Thr
2000                2005                2010

Leu Leu Thr Lys Gln Glu Thr Phe Asp Ala Gly Leu Gln Ala Phe
2015                2020                2025

Gln Gln Glu Gly Ile Ala Asn Ile Thr Ala Leu Lys Asp Gln Leu
2030                2035                2040

Leu Ala Ala Lys His Val Gln Ser Lys Ala Ile Glu Ala Arg His
2045                2050                2055

Ala Ser Leu Met Lys Arg Trp Ser Gln Leu Leu Ala Asn Ser Ala
2060                2065                2070

Ala Arg Lys Lys Lys Leu Leu Glu Ala Gln Ser His Phe Arg Lys
2075                2080                2085

Val Glu Asp Leu Phe Leu Thr Phe Ala Lys Lys Ala Ser Ala Phe
2090                2095                2100

Asn Ser Trp Phe Glu Asn Ala Glu Glu Asp Leu Thr Asp Pro Val
2105                2110                2115

Arg Cys Asn Ser Leu Glu Glu Ile Lys Ala Leu Arg Glu Ala His
2120                2125                2130

Asp Ala Phe Arg Ser Ser Leu Ser Ser Ala Gln Ala Asp Phe Asn
2135                2140                2145

Gln Leu Ala Glu Leu Asp Arg Gln Ile Lys Ser Phe Arg Val Ala
2150                2155                2160

Ser Asn Pro Tyr Thr Trp Phe Thr Met Glu Ala Leu Glu Glu Thr
2165                2170                2175

Trp Arg Asn Leu Gln Lys Ile Ile Lys Glu Arg Glu Leu Glu Leu
2180                2185                2190

Gln Lys Glu Gln Arg Arg Gln Glu Glu Asn Asp Lys Leu Arg Gln
2195                2200                2205

Glu Phe Ala Gln His Ala Asn Ala Phe His Gln Trp Ile Gln Glu
2210                2215                2220

Thr Arg Thr Tyr Leu Leu Asp Gly Ser Cys Met Val Glu Glu Ser
2225                2230                2235

Gly Thr Leu Glu Ser Gln Leu Glu Ala Thr Lys Arg Lys His Gln
2240                2245                2250

Glu Ile Arg Ala Met Arg Ser Gln Leu Lys Lys Ile Glu Asp Leu
2255                2260                2265

Gly Ala Ala Met Glu Glu Ala Leu Ile Leu Asp Asn Lys Tyr Thr
2270                2275                2280

Glu His Ser Thr Val Gly Leu Ala Gln Gln Trp Asp Gln Leu Asp
2285                2290                2295

Gln Leu Gly Met Arg Met Gln His Asn Leu Glu Gln Gln Ile Gln
2300                2305                2310

Ala Arg Asn Thr Thr Gly Val Thr Glu Glu Ala Leu Lys Glu Phe
2315                2320                2325

Ser Met Met Phe Lys His Phe Asp Lys Asp Lys Ser Gly Arg Leu
2330                2335                2340
```

Asn His Gln Glu Phe Lys Ser Cys Leu Arg Ser Leu Gly Tyr Asp
2345                2350                2355

Leu Pro Met Val Glu Gly Glu Pro Asp Pro Glu Phe Glu Ala
2360                2365                2370

Ile Leu Asp Thr Val Asp Pro Asn Arg Asp Gly His Val Ser Leu
2375                2380                2385

Gln Glu Tyr Met Ala Phe Met Ile Ser Arg Glu Thr Glu Asn Val
2390                2395                2400

Lys Ser Glu Glu Ile Glu Ser Ala Phe Arg Ala Leu Ser Ser
2405                2410                2415

Glu Gly Lys Pro Tyr Val Thr Lys Glu Glu Leu Tyr Gln Asn Leu
2420                2425                2430

Thr Arg Glu Gln Ala Asp Tyr Cys Val Ser His Met Lys Pro Tyr
2435                2440                2445

Val Asp Gly Lys Gly Arg Glu Leu Pro Thr Ala Phe Asp Tyr Val
2450                2455                2460

Glu Phe Thr Arg Ser Leu Phe Val Asn
2465                2470

<210> SEQ ID NO 4
<211> LENGTH: 1014
<212> TYPE: PRT
<213> ORGANISM: Homo sapiens

<400> SEQUENCE: 4

Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
                20                  25                  30

Leu Arg Met Ala Ile Met Val Gln Ser Pro Met Phe Asp Gly Lys Val
            35                  40                  45

Pro His Trp Tyr His Phe Ser Cys Phe Trp Lys Val Gly His Ser Ile
        50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

-continued

```
Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
        435                 440                 445

Ala Asn Ile Arg Val Val Ser Glu Asp Phe Leu Gln Asp Val Ser Ala
450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
        515                 520                 525

Gly Gly Ala Ala Val Asp Pro Asp Ser Gly Leu Glu His Ser Ala His
530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu His Phe Met Lys Leu Tyr Glu Lys Thr Gly Asn
610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655
```

-continued

```
Val Asn Pro Gly Thr Lys Ser Lys Leu Pro Lys Pro Val Gln Asp Leu
            660                 665                 670

Ile Lys Met Ile Phe Asp Val Glu Ser Met Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
            725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
            755                 760                 765

Leu Asp Ile Glu Val Ala Tyr Ser Leu Leu Arg Gly Gly Ser Asp Asp
    770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
            805                 810                 815

Tyr Val Lys Asn Thr His Ala Thr Thr His Asn Ala Tyr Asp Leu Glu
            820                 825                 830

Val Ile Asp Ile Phe Lys Ile Glu Arg Glu Gly Glu Cys Gln Arg Tyr
            835                 840                 845

Lys Pro Phe Lys Gln Leu His Asn Arg Arg Leu Leu Trp His Gly Ser
850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
            885                 890                 895

Phe Ala Asp Met Val Ser Lys Ser Ala Asn Tyr Cys His Thr Ser Gln
            900                 905                 910

Gly Asp Pro Ile Gly Leu Ile Leu Leu Gly Glu Val Ala Leu Gly Asn
            915                 920                 925

Met Tyr Glu Leu Lys His Ala Ser His Ile Ser Lys Leu Pro Lys Gly
    930                 935                 940

Lys His Ser Val Lys Gly Leu Gly Lys Thr Thr Pro Asp Pro Ser Ala
945                 950                 955                 960

Asn Ile Ser Leu Asp Gly Val Asp Val Pro Leu Gly Thr Gly Ile Ser
            965                 970                 975

Ser Gly Val Asn Asp Thr Ser Leu Leu Tyr Asn Glu Tyr Ile Val Tyr
            980                 985                 990

Asp Ile Ala Gln Val Asn Leu Lys  Tyr Leu Leu Lys Leu  Lys Phe Asn
            995                 1000                1005

Phe Lys  Thr Ser Leu Trp
1010
```